US007108995B2

(12) United States Patent
Despres et al.

(10) Patent No.: US 7,108,995 B2
(45) Date of Patent: Sep. 19, 2006

(54) SMALL PEPTIDES HAVING APOPTOTIC ACTIVITIES AND THEIR APPLICATIONS

(75) Inventors: Philippe Despres, La Garenne-Colombes (FR); Adeline Catteau, Savigny-sur-Orge (FR)

(73) Assignee: Institut Pasteur, Paris (FR)

( * ) Notice: Subject to any disclaimer, the term of this patent is extended or adjusted under 35 U.S.C. 154(b) by 458 days.

(21) Appl. No.: 10/608,147

(22) Filed: Jun. 30, 2003

(65) Prior Publication Data

US 2005/0080231 A1 Apr. 14, 2005

Related U.S. Application Data

(63) Continuation-in-part of application No. 10/311,213, filed as application No. PCT/IB01/01570 on Jun. 18, 2001.

(51) Int. Cl.
*G01N 33/53* (2006.01)
*C07K 7/06* (2006.01)

(52) U.S. Cl. ........................ 435/7.8; 530/328; 530/329

(58) Field of Classification Search ..................... None
See application file for complete search history.

*Primary Examiner*—Robert A. Wax
(74) *Attorney, Agent, or Firm*—Oblon, Spivak, McClelland, Maier & Neustadt, P.C.

(57) ABSTRACT

The present invention relates to nine residue peptides ($M^{32-40}$) from flavivirus M ectodomain able to modulate specifically the apoptotic activity of diverse flavivirus, to pharmaceutical composition comprising the same and their use for the treatment and/or the prevention of flavivirus-linked infections and cancers.

7 Claims, 18 Drawing Sheets

Figure 1:
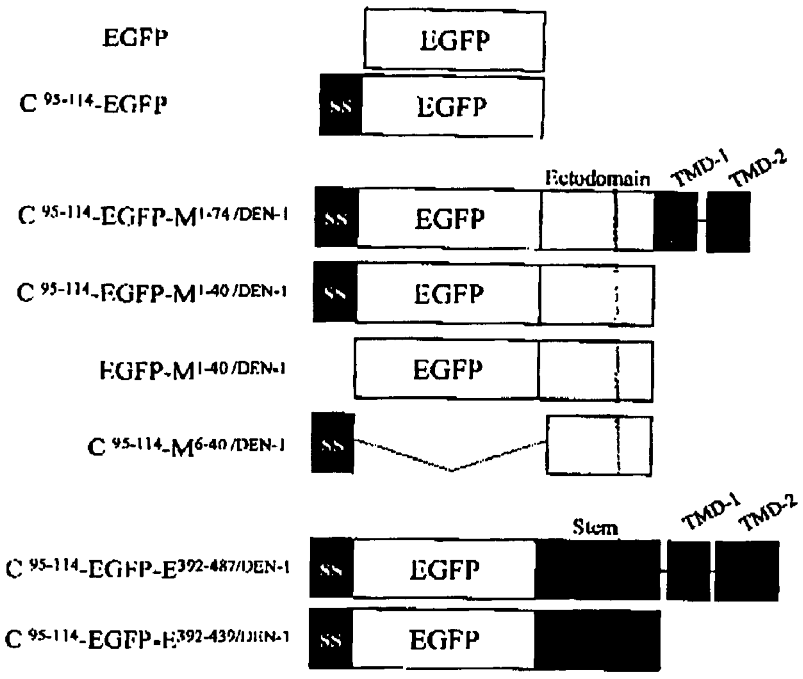

A.
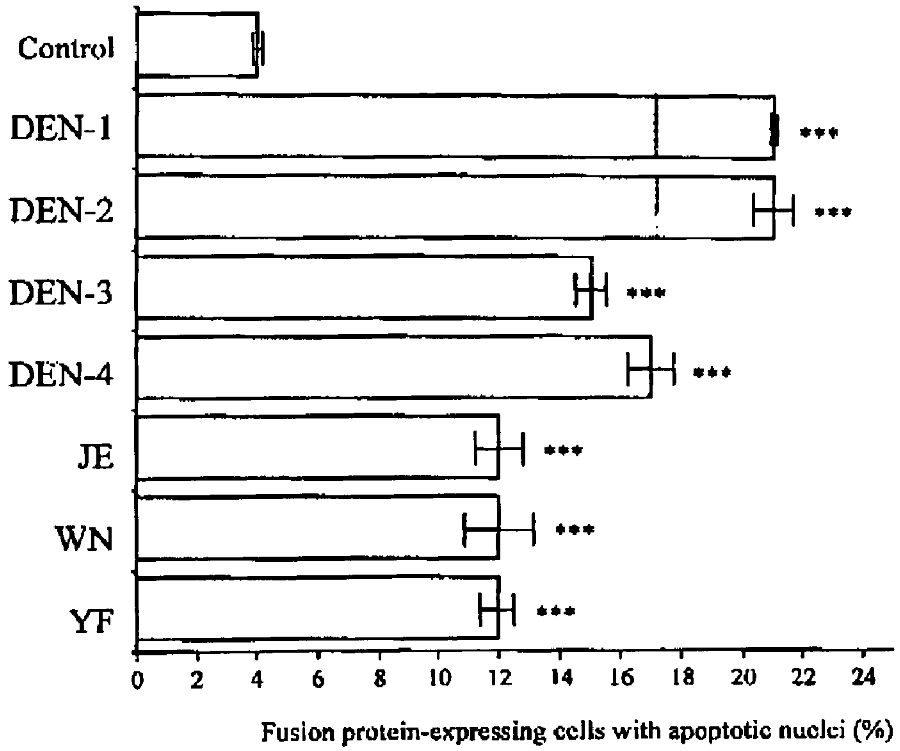
B.
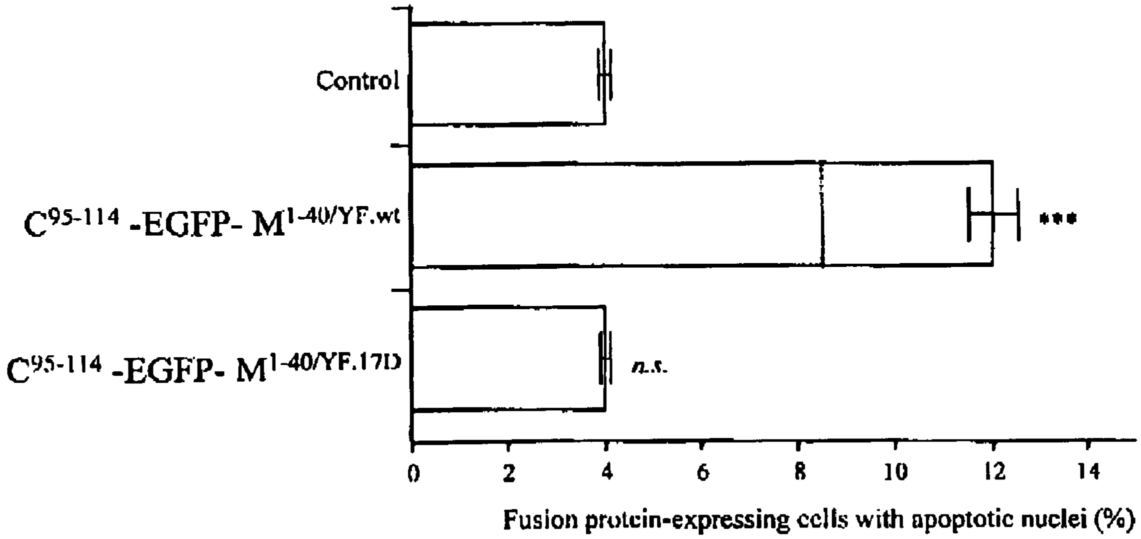
FIGURE 4

| | DEN-2 *ectoM* mutants |
|---|---|
| $^{1}$SVALVPHVGMGLETRTETWMSSEGAWKHVQRIETWILRHP$^{40}$ | $M^{1\text{-}40/DEN\text{-}2}$ |
| $^{1}$SVALVPHVGMGLETRTETWMSSEGAWKHVQ$^{30}$ | $M^{1\text{-}30/DEN\text{-}2}$ |
| $^{1}$SVALVPHVGMGLETRTETWM$^{20}$ | $M^{1\text{-}20/DEN\text{-}2}$ |
| $^{10}$GMGLETRTETWMSSEGAWKHVQ$^{30}$ | $M^{10\text{-}30/DEN\text{-}2}$ |
| $^{10}$GMGLETRTETWMSSEGAWKHVQRIETWILRHP$^{40}$ | $M^{10\text{-}40/DEN\text{-}2}$ |
| $^{20}$MSSEGAWKHVQRIETWILRHP$^{40}$ | $M^{20\text{-}40/DEN\text{-}2}$ |
| $^{32}$IETWILRHP$^{40}$ | $M^{32\text{-}40/DEN\text{-}2}$ |

*FIG. 5A*

A.

ecto-M
```
         *  *    ** **  *  **           *  ** *   *   *
¹AIDLPTHENHGLKTRQEKWMTGRMGERQLQKIERWFVRNP⁴     M ¹⁻⁴⁰/YF.17D
¹----------------------------------T-IL-H-     M ¹⁻⁴⁰/YF.17D (T³⁴, I³⁶, L³⁷, H³⁹)

¹SVALVPHVGMGLETRTETWMSSEGAWKHVQRIETWILRHP⁴     M ¹⁻⁴⁰/DEN-2
¹---------------------------------F----        M ¹⁻⁴⁰/DEN-2 (F³⁶)
```

B.

| | |
|---|---|
| Control | |
| $M^{1-40/YF.17D}$ | n.s. |
| $M^{1-40/YF.17D}(T^{34}, I^{36}, L^{37}, H^{39})$ | *** |
| $M^{1-40/DEN-2}$ | *** |
| $M^{1-40/DEN-2}(F^{36})$ | *** |

Fusion protein-expressing cells with apoptotic nuclei (%)

```
SVALAPHVGLGLETRTETWMSSEGAWKQIQKVETWALRHP DEN-1
----V----M-----------------HA-RI---I---- DEN-2
---------M--D---Q----A----R-VE---------- DEN-3
----T--S-M-----A-----------HA-R--S-I--N- DEN-4
AID-PT-ENH--K--Q-K--TGRMGER-L--I-R-FV-N- YFV 17D
-LTVQT-GEST-ANKKGA--D-TK-TRYLV-T-S-I--N- WNV
--SVQT-GESS-VNKKEA-LD-TK-TRYLM-T-N-IV-N- JEV
```

Sub-sequence of 9 aminoacids

GenBank Acession Number (DEN-1) AAB27904

$^{206}$SVALAPHVGLGLETRTETWMSSEGAWKQIQK$^{236}$ $^{237}$VETWALRHP$^{245}$

```
1-----------------------------31     32-------40
----V----M-----------------HA-R      I---I----     DEN-2
---------M--D---Q----A----R-VE-      ---------     DEN-3
----T--S-M-----A-----------HA-R      --S-I--N-     DEN-4
AID-PT-ENH--K--Q-K--TGRMGER-L--      I-R-FV-N-     YFV 17D
-LTVQT-GEST-ANKKGA--D-TK-TRYLV-      T-S-I--N-     WNV
--SVQT-GESS-VNKKEA-LD-TK-TRYLM-      T-N-IV-N-     JEV
```

FIGURE 10

SMALL PEPTIDES HAVING APOPTOTIC ACTIVITIES AND THEIR APPLICATIONS

This application is a continuation-in-part of application Ser. No. 10/311,213, May 19, 2003, which is an application filed under 35 USC 371 of PCT/IB01/01570, filed Jun. 18, 2001 which claims benefit of provisional application Serial No. 60/212,129, filed Jun. 16, 2000.

The present invention relates to small peptides of a length of at most nine amino acids from flavivirus M32–40 ectodomain able to induce apoptosis in target cells such as infected cells or cancer cells, to nucleic acid molecules containing said peptides, to pharmaceutical compositions comprising the same and their use for the treatment and/or the prevention of infections and cancers.

Mosquito-borne flaviviruses such as the dengue (DEN), Japanese encephalitis (JE), Saint Louis encephalitis (SLE), West Nile (WN) and yellow fever (YF) viruses may cause epidemic disease outbreaks in humans. Infected patients may exhibit a wide range of acute diseases, from nonspecific febrile illness to severe hemorrhagic manifestations (DEN and YF) or encephalitic syndromes (JE, SLE and WN). Flaviviruses (family Flaviviridae) are single-stranded, enveloped RNA viruses (5, 41). The virion consists of three structural proteins: C (core protein), M (membrane protein) and E (envelope protein) (5, 41). The translation of genomic RNA generates a large polyprotein precursor, which is cotranslationally processed by host cell- and virus-encoded proteases to yield the individual structural and non-structural viral proteins. The structural proteins are C, prM (the intracellular precursor of M), and E (5, 41). E and prM are both type I transmembrane glycoproteins (5, 41). The prM glycoprotein consists of a long ectodomain followed by a transmembrane-anchoring region (5, 41). The carboxy-terminal region of the prM protein gives rise to the small membrane (M) protein (7–9 kDa). The mature M protein consists of a 40 amino acid ectodomain followed by the transmembrane-anchoring region including two transmembrane domains (TMDs) (5, 41). The E protein consists of a long ectodomain followed by a stem-anchor region (5, 41). The first steps of flavivirus assembly take place in association with the membranes of the endoplasmic reticulum (ER). The virion is first assembled as an immature particle, in which prM is non-covalently associated with E in a heterodimeric complex. Late in virus morphogenesis, prM is processed by subtilisin-like proteases to generate the mature M protein in the exocytic pathway of the trans-Golgi network (5, 41). Three-dimensional imaging of the structure of the DEN virion, showing the location of the M protein with respect to the E homodimer, was recently carried out (25). Several studies have shown that the M ectodomain induces a neutralizing antibody response (3, 47).

Recent advances in cell biology have resulted in advances in our understanding of the mechanisms of virus-induced cell death, which determine the outcome of flavivirus infection (36, 37, 39, 42, 45). Cytotoxicity seems to result from apoptosis, which may contribute to the clinical manifestations associated with flavivirus infection (8, 13). Apoptosis is an active process of cell death involving a number of distinct morphological changes including cell shrinkage, phosphatidyl-serine (PS) externalization, fragmentation of the cell nucleus, chromatin condensation, protein cross-linking and apoptotic body formation (21, 24). Apoptosis is induced via the activation of intracellular signaling systems, a number of which converge on mitochondrial membranes to induce their permeabilization (21, 24). The morphological and biochemical changes associated with apoptosis are orchestrated by the activity of a family of cysteine proteases called caspases (14, 41). Mitochondria membrane permeabilization plays an essential role in apoptosis, releasing caspase-activating proteins that are normally confined to the mitochondrial intermembrane space (2, 9, 21). Members of the Bcl-2 family have been shown to exhibit both anti-apoptosis and proapoptotic activities (1). For example, increased levels of Bcl-2 lead to cell survival whereas excess of Bax is associated with apoptosis.

All four serotypes of DEN virus (DEN-1, DEN-2, DEN-3, and DEN-4), and the JE, SLE, WN, and YF viruses have been reported to trigger apoptosis in host cells (36, 37, 39, 42, 45). The precise mechanisms by which flaviviruses induce the death of infected cells are unclear, but it is thought that virus infection may activate biochemically different apoptotic pathways converging in the modification of mitochondrial function. The intracellular production of viral proteins has been shown to be essential for the induction of apoptosis by flaviviruses (12–14, 39, 40). The E and NS3 proteins may be involved in the induction of apoptosis by the tick-borne flavivirus Langat (39, 40). Detailed studies of molecular interactions between DEN-1 virus and host cells have led to the identification of viral proteins that may influence DEN virus-induced apoptosis (14).

WO 01/96376 discloses a pro-apoptotic fragment of 40 amino acids (ectodomain) from the dengue virus M protein and corresponding to residues 206–245 of said M protein. Said fragment, -included in a plasmid, p[95–114]EGFP [206–245], encompassing the DEN-1 virus strain BR/90 encoding the C protein residues 95 to 114 upstream of the EGFP gene and the sequence of the DEN-1 virus strain FGA/89, encoding the M protein residues 206 to 245 downstream of the EGFP gene-, induces rapid apoptosis in Neuro 2a, HepG2, HeLa and Vero cells as early as 20 hours post-transfection.

WO 01/96376 describes also a series of deletion variants of said 40 amino acids protein M ectodomain, which were constructed in view to find the elements which contribute to the efficient death-inducing activity of the M ecto-domain. The results obtained with said variants show that transient expression of the deletion variants of the chimeric protein [95–114]EGFP[206–245]DEN-2 demonstrated that amino acids M10 to M40 of the M ectodomain ([95–114]EGFP [M10->M40]DEN-2) significantly contribute to the efficient formation of the fluorescent mass in the secretory pathway.

Figure 12:
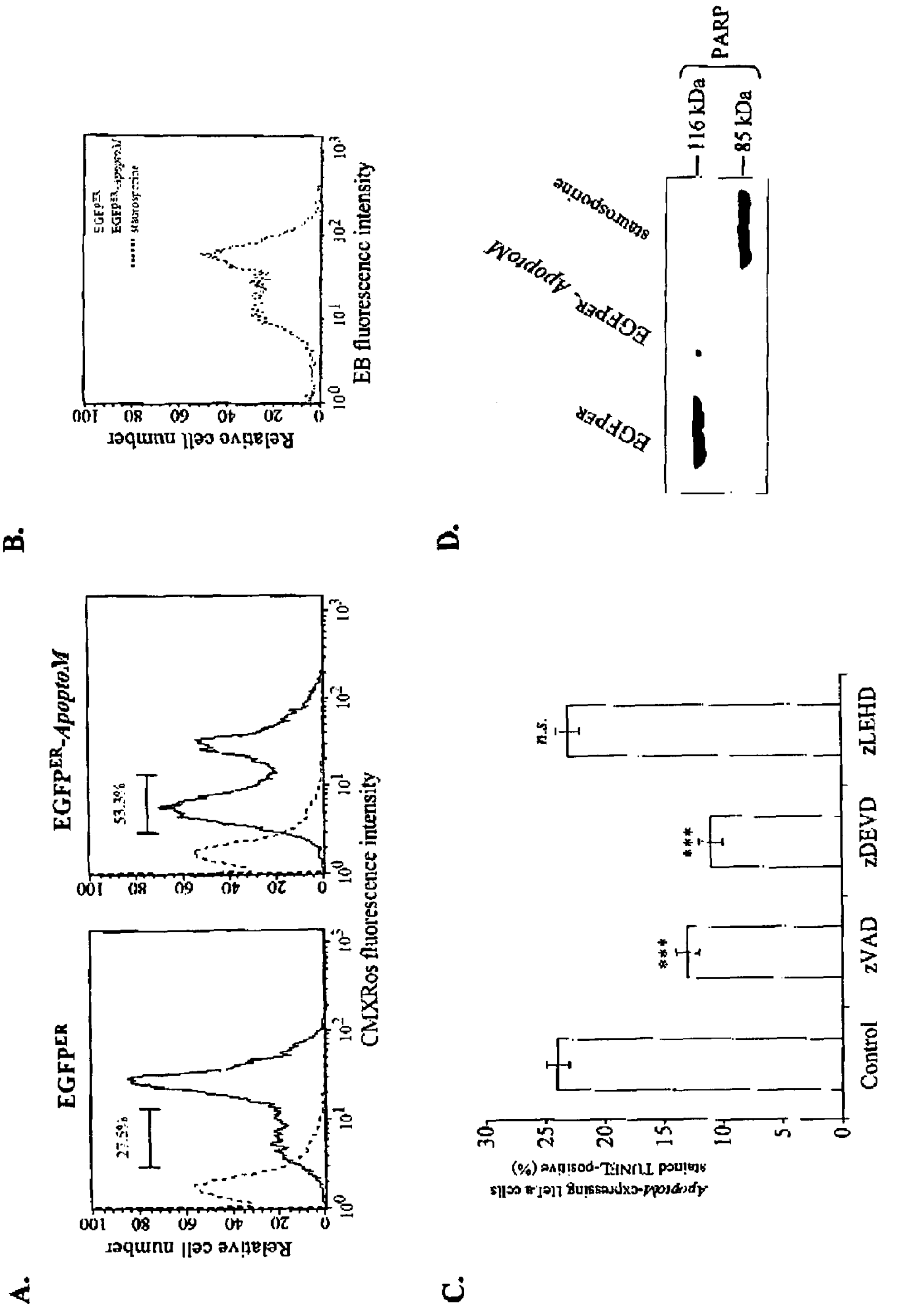

However, the deletion variant corresponding to the 10 amino acids C-terminal fragment of the M ectodomain (FIG. 12 of WO 01/96376) does not present apoptotic properties.

Pursuing their works, the Inventors have now found unexpectedly that much smaller fragments, i.e. of less than 10 amino acids from the C-terminal part of said M ectodomain induce apoptosis and may therefore be used in cancer therapy compositions.

Such small fragments have the following advantages:

To be easy to prepare and to be produced easily in large quantities.

Not to be too costly and

They are very short peptides, so they can readily enter into the cell.

Surprisingly, the Inventors have found that, when truncated forms of the DEN-2 M ectodomain are assayed for their ability to induce apoptosis, fragments of the nine carboxy-terminal amino acids of the M ectodomain (M32–M40) comprising between 6 and 9 amino acids constitute a pro-apoptotic sequence.

More specifically, by comparing the sequence homology of the M ectodomains from:

four serotypes of DEN (DEN-1 to DEN-4),

YF vaccine strain 17D which is known to have lost the ability to cause viscerotropic disease, WN virus, and JE virus, the inventors have determined a consensus pro-apoptotic peptide which covers combinations of 6–9 amino acid residues having pro-apoptotic activity and therefore conferring pathogenicity to flavivirus.

Therefore, the present invention relates to an isolated and purified peptide, characterized in that it has the following formula:

X1-X2-X3-X4-X5-X6-X7-X8-X9, wherein:

X1 is absent or represents an amino acid selected in the group consisting of non-charged polar amino acids and non-polar amino acids, X2 is absent or represents an amino acid selected in the group consisting of acidic amino acids, non-charged polar amino acids and non-polar amino acids, X3 is selected in the group consisting of basic amino acids, non-charged polar amino acids and non-polar amino acids, X4 is W, X5 represents an amino acid selected in the group consisting of A, V, L, I, P, W, M and C, X6 is selected in the group consisting of non-polar amino acids, X7 is a basic amino acid X8 is selected in the group consisting of basic amino acids and non-charged polar amino acids and X9 is absent or represents an amino acid selected in the group consisting of basic amino acids and non-polar amino acids.

The amino acids (or amino acid residues) described herein are preferred to be in the "L" isomeric form. However, residues in the "D" isomeric form can be substituted for any L-amino acid residue, as long as the desired functional property is conserved. In keeping with standard polypeptide nomenclature, *J. Biol. Chem.,* 243:3552–59 (1969), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |

-continued

TABLE OF CORRESPONDENCE

| SYMBOL | | |
|---|---|---|
| 1-Letter | 3-Letter | AMINO ACID |
| R | Arg | arginine |
| D | Asp | aspartic acid |
| N | Asn | asparagine |
| C | Cys | cysteine |

It should be noted that all amino acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

The following gives the list of the amino acids in each of the group specified here above:

Amino acids with non-polar R groups

Alanine, Valine, Leucine, Isoleucine, Proline, Phenylalanine, Tryptophan, Methionine, Cysteine Amino acids with uncharged (or non-charged) polar R groups Glycine, Serine, Threonine, Tyrosine, Asparagine, Glutamine Amino acids with charged polar R groups (acid amino acids) (negatively charged at pH 6.0)

Aspartic acid, Glutamic acid

Basic amino acids (positively charged at pH 6.0)

Lysine, Arginine, Histidine (at pH 6.0).

Particularly preferred conservative substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

According to an advantageous embodiment of the invention, said peptide is selected in the group consisting of the following peptides:

Peptides of 6–9 amino acids wherein X5=I, L, A;

Peptides of 6–9 amino acids, wherein X1 is absent or represents I, V, T, X2 is absent or represents E, X3=T, S, R, N, X4=W, X5=I, A, X6=L, V, X7=R, X8=H, N, X9 is absent or represents P;

Peptides of 6–9 amino acids, wherein X3=T, X5=I, X6=L and X8=H.

According to another advantageous embodiment of the invention, said peptide is selected in the group consisting of the following peptides:

Peptides of 6–9 amino acids wherein X5=I, L, A;

Peptides of 6–9 amino acids, wherein X1 is absent or represents I, V, T, X2 is absent or represents E, X3=T, S, R, N, X4=W, X5=I, A, X6=L, V, X7=R, X8=H, N, X9 is absent or represents P;

Peptides of 6–9 amino acids, wherein X3=T, X5=I, X6=L and X8=H, with the proviso that said peptide is not the peptide having the following sequence: IETWILRHP (SEQ ID NO:29).

According to another advantageous embodiment of the invention, said peptide has the following sequence: IETWILRHP (SEQ ID NO:29.

The invention also includes any functional derivative of the peptides as defined above, comprising one or more modifications which do not affect substantially the biological activities of the initial peptide.

Such modifications include for example: replacement of one or more of the amide bond by a non-amide bond, and/or replacement of one or more amino acid side chain by a different chemical moiety, and/or protection of the N-terminus, the C-terminus, or one or more of the side chain by a protecting group, and/or introduction of double bonds and/or cyclization and/or stereospecificity into the amino acid chain to increase rigidity, and/or binding affinity and/or enhance resistance to enzymatic degradation of the peptides. Since all the variations are known in the art, it is submitted that a person skilled in the art will be able to produce, test, identify and select other peptides according to the present invention. For instance, in some cases it may be possible to replace a residue in the L-form by a residue in the D-form or the replacement of the glutamine (Q) residue by a pyro-glutaminic acid compound.

The peptides according to the invention refer to peptides which have the following activities:

- biological activity: they have a pro-apoptotic activity;
- antibody binding activity: they are recognized specifically by an anti-$M^{32-40}$ monoclonal or polyclonal antibody, which may be induced, preferably with a peptide as defined hereabove conjugated with a carrier protein such as BSA (bovine serum albumin) or KLH (keyhole limpet haemocyanin).

The biological activity of the instant peptides can be verified by in situ detection of apoptotic cells and/or by flow cytometry of early apoptosis and/or ELISA assay, which are well-known by a person skilled in the art. These techniques can be performed for example on transformed or tumor cell lines such as HeLa cells which are initially transfected by a recombinant vector containing the sequence encoding prM translocation signal fused in frame with the sequence encoding the N-terminal fragment of the enhanced green fluorescent protein (EGFP) and downstream the sequence encoding a peptide according to the invention and appropriate regulation sequences.

The instant peptides which may be active in vivo or in vitro are useful:

- for treating patients with cancers,
- for producing monoclonal antibodies to be used as a diagnostic tool in the detection of flavivirus infections in a biological sample; moreover, knowing that the instant peptides correspond to a conserved sequence in the flavivirus phylogeny, the obtained antibodies may advantageously be used for the detection of flavivirus, whatever the variant.

In addition to said therapeutic use, the instant peptides are useful as complementary tools to uncover mechanisms of action and unknown function of the M ectodomain of flavivirus.

According to the invention, said peptide may be associated with or conjugated to another peptide or protein such as a carrier protein as defined hereabove or non-peptide molecule and/or incorporated into a suitable support including for example, polymers, lipidic vesicles, microspheres, proteins and the like. Such association which may improve the penetration of the instant peptide in the target cell, is formed, by using techniques well-known in the art; it may be through, without limitation, covalent bonding (e.g., amide bond, disulfide bond . . . ), or through chelation, electrostatic interactions, hydrophobic interactions, hydrogen bonding, ion-dipole interactions, dipole-dipole interactions, or any combination of the above.

The peptide of the present invention may be prepared by any suitable process. Preferably, it is obtained by chemical synthesis in liquid or solid phase by successive couplings of the different amino acid residues to be incorporated (from the N-terminal end to the C-terminal end in liquid phase, or from the C-terminal end to the N-terminal end in solid phase) wherein the N-terminal ends and the reactive side chains are previously blocked by conventional groups. For solid phase synthesis the technique described by Merrifield (J. Am. Chem. Soc., 1964, 85, 2149–2154) may be used.

The peptide of the present invention may also be obtained by genetic engineering technology. A typical example comprises culturing a host cell containing an expression vector comprising a nucleic acid sequence encoding said peptide, under conditions suitable for the expression of the peptide, and recovering the peptide from the host cell culture. The peptide may be included in a fusion protein by cloning a cDNA into an expression vector in frame with a polynucleotide coding for the peptide of the invention. Alternatively, multimer of identical or different peptides can also be produced by expressing a polynucleotide coding for multiple copies of a monomer, or coding for different monomers.

Thus, the invention also provides a polynucleotide encoding a peptide according to the invention, as well as the complement of said polynucleotide.

Definitions

The positions of the M ectodomain are given in reference either to DEN-1 M ectodomain or to DEN-1 M protein; therefore, positions 237–245 are equivalent to positions 32–40 (see FIG. 10). Hereafter, peptides $M^{32-40}$ may be designated $M^{32-40}$.

An apoptotic molecule is a molecule which influences or modifies apoptosis.

A pro-apoptotic molecule is a molecule which induces apoptosis (directly or indirectly).

An anti-apoptotic molecule is a molecule which inhibits apoptosis (directly or indirectly).

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes.

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide" is defined as a molecule comprising two or more ribonucleotides, preferably more than three. Its exact size will depend upon many factors which, in turn, depend upon the ultimate function and use of the oligonucleotide.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., SAMBROOK et al., "Molecular Cloning: A Laboratory Manual" (1989); "Nucleic Acid Hybridization" [B. D. Hames & S. J. Higgins eds. (1985)]; B. Perbal, "A practical Guide To Molecular Cloning" (1984).

It should be appreciated that also within the scope of the present invention are the biological uses of the DNA sequences encoding said peptides, but which are degenerate to the DNA encoding said peptides. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Therefore, the invention provides the nucleotide sequences encoding the peptides as defined here above, including all possible examples of nucleotide sequences encoding these peptides which result from the degeneration of the genetic code.

Nucleic acids of the invention may be obtained by the well-known methods of recombinant DNA technology and/or chemical DNA synthesis.

The invention also provides recombinant vectors comprising a polynucleotide encoding a peptide of the invention.

Vectors of the invention are preferably expression vector with a specific targeting through the secretory pathway, wherein a sequence encoding a peptide of the invention is associated to a sequence encoding a secretory pathway targeting protein, said combined sequence, encoding a fusion protein able to allow expression of said peptide in the secretion pathway and being placed under control of appropriate transcriptional and translational control elements.

These vectors may be obtained and introduced in a host cell by the well-known recombinant DNA and genetic engineering techniques, as specified in the here above definitions.

According to another preferred embodiment of the invention, said recombinant vector contains a marker such as a fluorescent marker, to facilitate the detection of the peptides according to the invention.

According to another preferred embodiment of the invention, said sequence encoding a secretory pathway targeting protein is selected in the group consisting of a sequence encoding an endoplasmic reticulum targeting signal peptide such as a translocation signal peptide and more specifically the prM translocation signal peptide corresponding to fragment 95–114 of the C protein of a flavivirus and more preferably of a dengue (DEN) virus and a membrane-anchoring signal peptide that targets glycoproteins to the plasma membrane, such as the fragment 1-118 of CD72 (cytosolic tail of a type II integral membrane glycoprotein).

Such a construction allows the transport of the peptide of the instant invention through the secretory pathway, which is essential for the induction of the apoptosis.

Preferably, said recombinant vector contains a polynucleotide encoding the peptide having the following sequence: IETWILRHP and corresponds to the following plasmids:

- plasmid p[95–114]EGFP[237–245]DEN-2, which has been deposited at the Collection Nationale de Cultures de Microorganismes, 28 Rue de Docteur Roux, F-75724 Paris Cedex 15, on Mar. 29, 2002 under the number I-2829. Said plasmid contains the sequence encoding the C-terminal 20 amino acids of the BR/90 C protein (residues 95 to 114), which function as a sequence signal to direct the translocation of prM onto the lumen of ER, this sequence signal being inserted upstream from sequences encoding the EGFP-tagged M peptide.
- plasmid Trip ΔU3 CMV [95-114]EGFP[237–245]DEN-2, which has been deposited at the Collection Nationale de Cultures de Microorganismes, 28 Rue de Docteur Roux, F-75724 Paris Cedex 15, on May 23, 2003, under the number I-3032. Plasmids including retroviral vectors of the TRIP type are, for instance, described in the French Patent FR 2 777 909.

The invention also comprises a prokaryotic or eukaryotic host cell transformed by a vector of the invention.

The invention further concerns polyclonal and monoclonal antibodies, and preferably monoclonal antibodies, raised specifically against the peptides of the instant invention and their utilization for prevention of disease and diagnostic purposes. Antibodies which react specifically with the instant peptides are generated by using methods well-known in the art. Examples of such methods are disclosed in Antibodies, A Laboratory Manual, Harlow and Lane, Cold Spring Harbor Press, 1988. Such antibodies have the advantage to recognize any flaviviruses, whatever the variant to be detected.

The invention further concerns a pharmaceutical composition comprising an effective amount, for inducing apoptosis in cancer cells, of a pro-apoptotic peptide or polynucleotide encoding the same of the invention, a targeting substance to the target cells and at least one pharmaceutically acceptable carrier.

According to the invention, said targeting substance may be any ligand which can bind specifically to the target cells.

Such compositions may be useful for treating patients with cancer, and in particular, by specifically targeting cancers cells and inducing apoptosis in those cancer cells.

The preferred frequency of administration and effective dosage will vary from one subject to another.

In vitro, the concentrations which can be used are comprised between 1 and 100 μM, preferably between 5 and 20 μM.

The optional carriers of the pharmaceutical compositions of the invention can be any vehicle for parenteral, oral, aerosol, nasal or ocular administration of drugs depend on the cancer to be treated. When the composition includes a polynucleotide, as defined here above, it may preferably include, for a better internalization of said polynucleotide, calcium phosphate, DEAE-Dextran, liposomes, viral vectors, etc. These and other methods of introducing polynucleotides into cells are disclosed in Sambrook et al., Molecular Cloning: A Laboratory Manual, Cold Spring Harbor Laboratory, New York (1989).

The present invention further includes methods of screening for molecules which modulate the cytotoxic activity of the pro-apoptotic fragments as defined here above. This method includes:

- introducing a peptide according to the invention, a polynucleotide according to the invention or a recombinant vector according to the invention into a cell,
- contacting said cell with the molecule to be screened and detecting the presence or absence of apoptosis.

Molecules to be screened can be proteins or any other organic or inorganic substance which may be found to inhibit apoptosis mediated by the instant peptides.

Such screened molecules may be useful to either treat flavivirus infections (inhibition of apoptosis) or to treat cancers (synergy of action with the pro-apoptotic peptides of the invention).

The invention further concerns the use of a peptide, a polynucleotide or a recombinant vector of the invention for the preparation of a medicament for the prevention and/or the treatment of cancers.

The invention further concerns the direct detection method of a flavivirus infection, which comprises:

- contacting a biological sample to be analysed or a culture medium supposed to eventually contain flavivirus antigens with antibodies according to the invention, optionally labelled, and
- detecting the antigen-antibody complex eventually formed by any means.

The invention further concerns the serological detection of a flavivirus infection, which comprises:

- contacting a biological sample with a solid support on which peptides according to the invention are bound, and
- detecting the eventually formed antigen-antibody complexes by any means.

The present invention will be further illustrated by the additional description and drawings which follow, which refer to examples illustrating the the properties of the instant peptides. It should be understood however that these examples are given only by way of illustration of the invention and do not constitute in anyway a limitation thereof.

FIG. 1 illustrates a schematic representation the EGFP-tagged DEN-1 proteins. The fusion proteins consisting of the ER targeting sequence ($C^{95-114}$, designed SS) of prM, the full-length M ($M^{1-74}$), the ectodomain ($M^{1-40}$) of the M protein, the stem-anchor ($E^{392-487}$) and the stem ($E^{392-487}$) of the E protein fused to EGFP, are depicted. The transmembrane domain (TMD) is shown. The fusion proteins are not drawn to scale. The names of fusion proteins are indicated on the left.

Figure 2A:
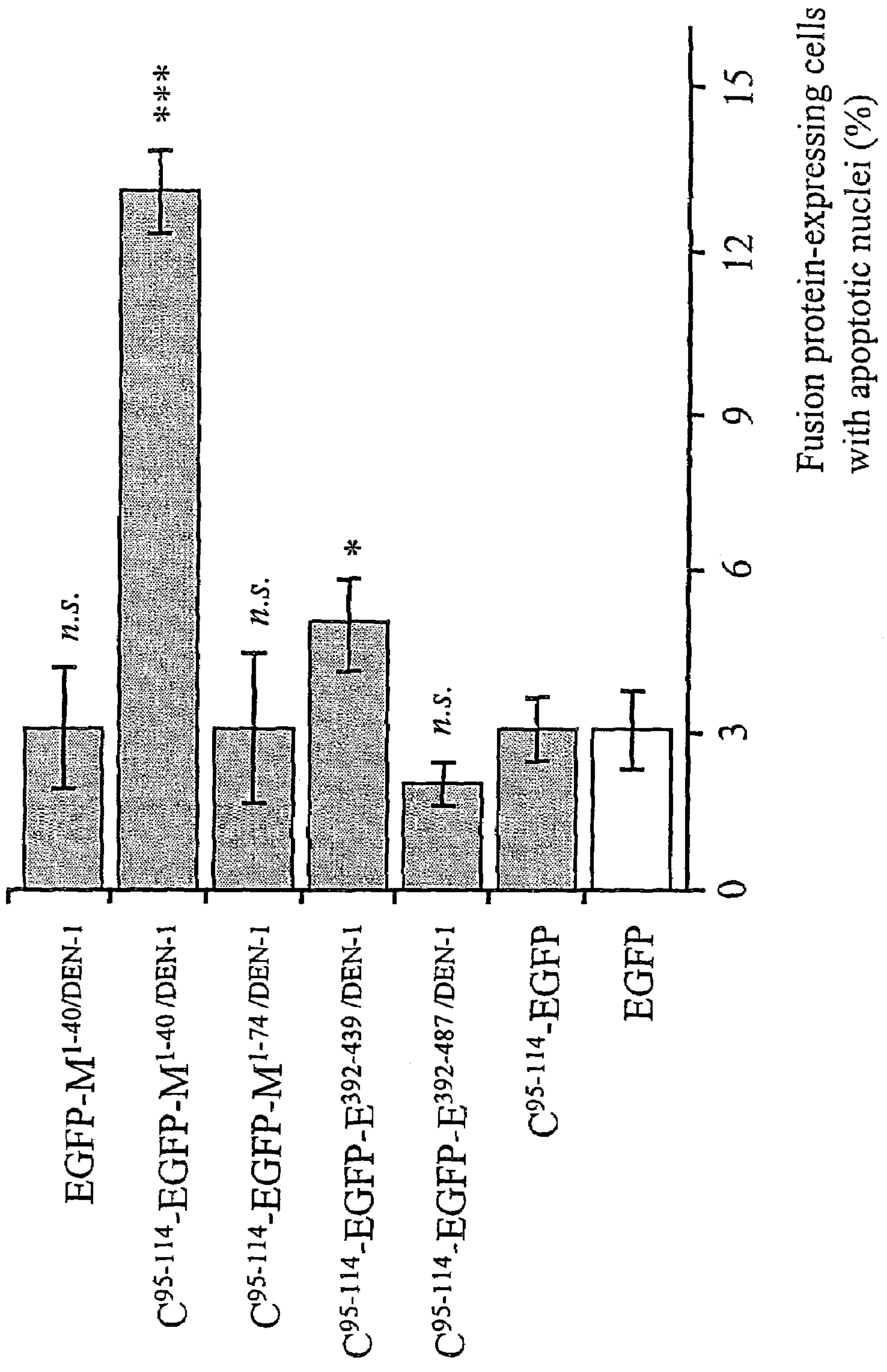
Figure 2B:
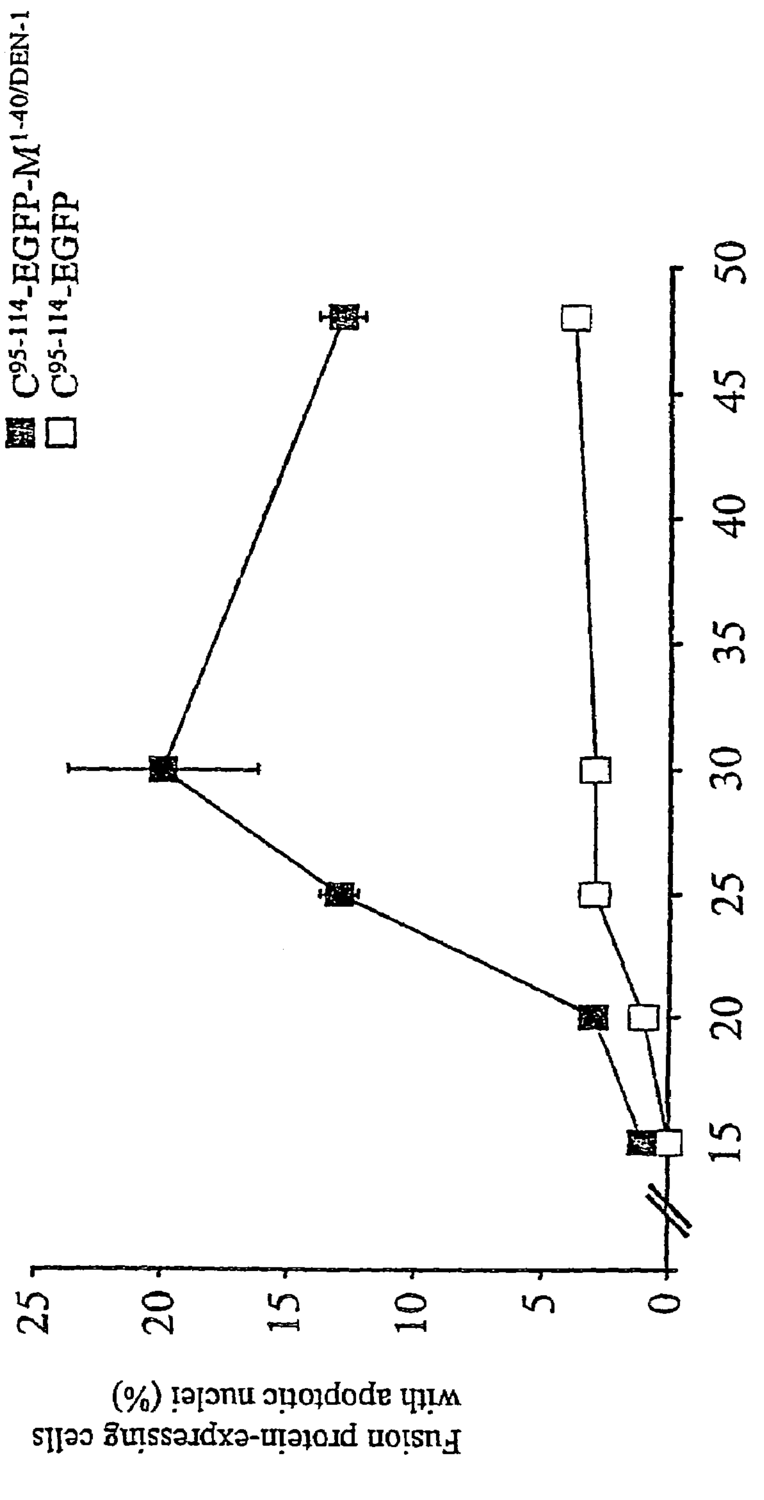
Figure 2C:
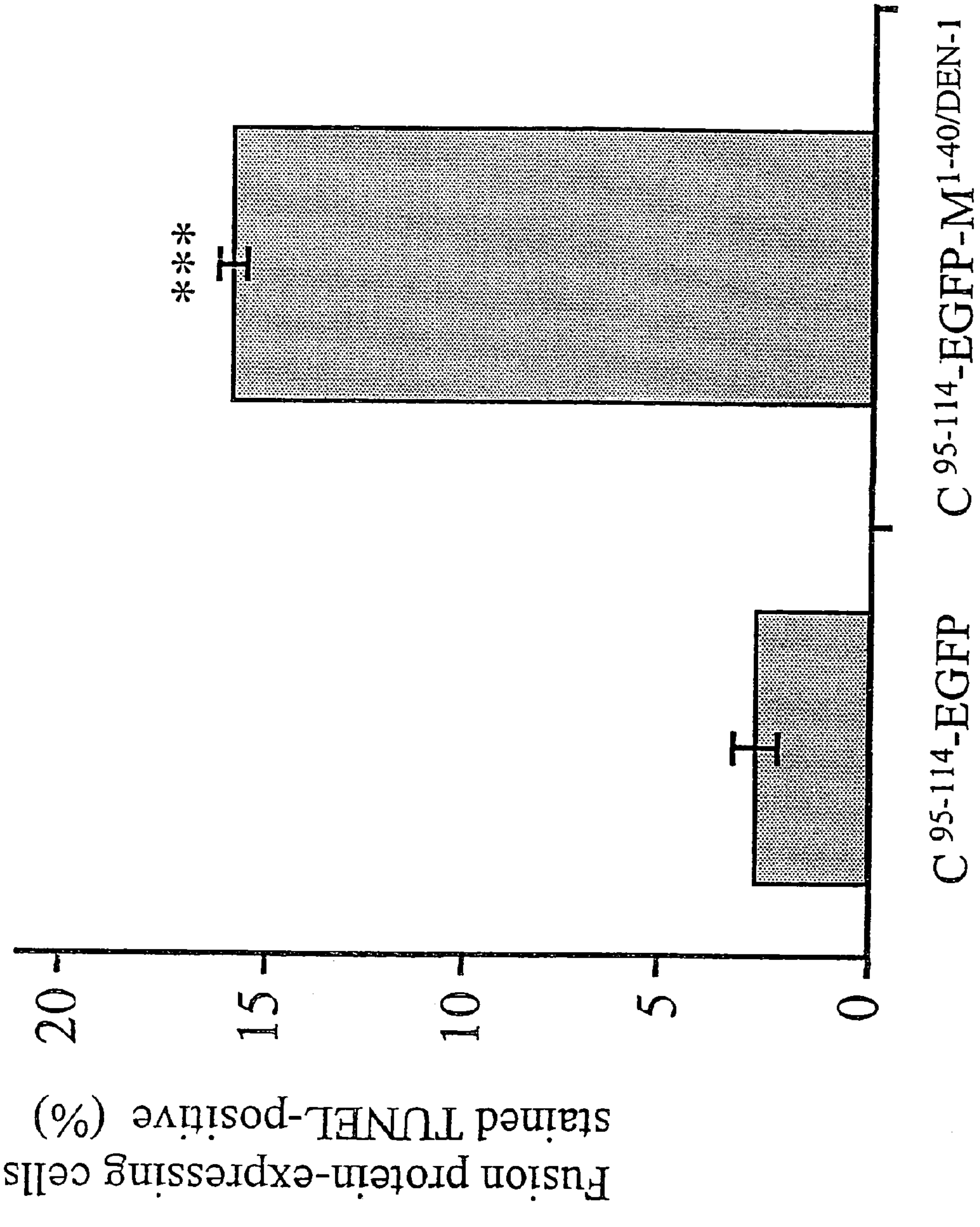

FIG. 2A–C shows that DEN-1 M ectodomain has proapoptotic activity. HeLa cells were transfected with plasmids encoding the fusion proteins described in FIG. 1. Transiently transfected HeLa cells were harvested after 25 hours (A and C) or at the times indicated (B). Fixed cells were stained with Hoechst 33258 (A and B) or assayed by TUNEL (C). Fusion proteins were detected by monitoring the autofluorescence of EGFP. Fusion protein-expressing cells with nuclear DNA nicks were monitored by TUNEL assay. Each experimental point represents the mean±the standard deviation (SD) of results obtained from three separate chambers. Fusion proteins were compared statistically with $C^{95-114}$-tagged EGFP: not significant (n.s., P>0.05) or significant (* P<0.05;  P<0.01;* P<0.001), according to Fisher and Yates's t tests.

Figure 3:
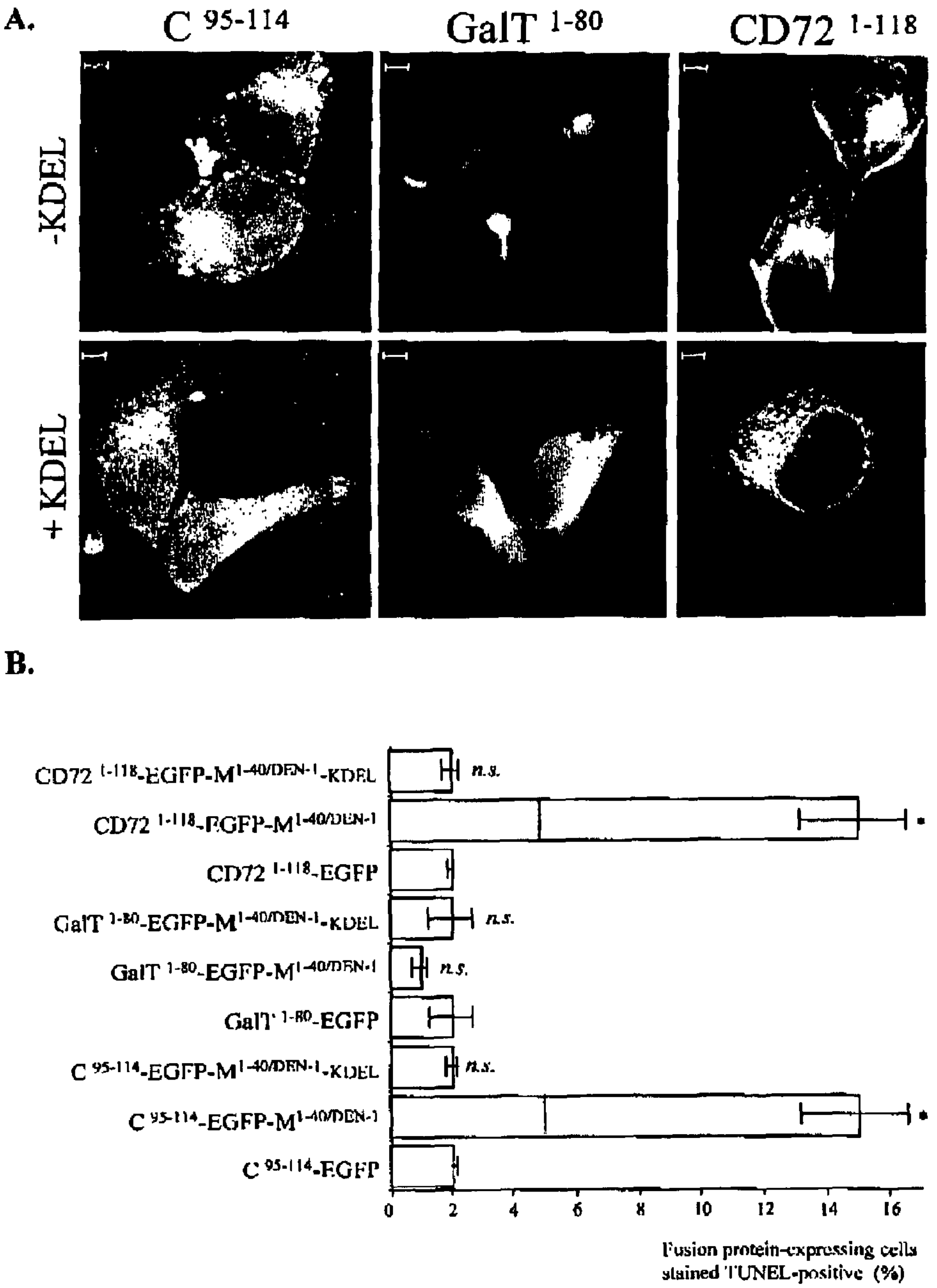

FIG. 3A–B illustrates the subcellular localization of the M ecto-domain. Transfected HeLa cells producing EGFP-tagged $M^{1-40/DEN-1}$ fusion proteins that contained either the prM translocation signal ($C^{95-114}$), the membrane-anchoring signal peptide of GalT ($GalT^{1-80}$), or the membrane-anchoring signal peptide of CD72 ($CD72^{1-118}$) in the presence (+KDEL) or in absence (−KDEL) of ER retrieval KDEL sequence were detected by monitoring the autofluorescence of EGFP (A) or analyzed for apoptosis (B). (A) Transfected cells were examined by fluorescence microscopy. The scale bar represents 0.5 μm. (B) Nuclear DNA nicks of transfected cells were monitored by TUNEL assay after 30 hours of transfection. $C^{95-114}$-EGFP, $GalT^{1-80}$-EGFP and $CD72^{1-118}$-EGFP served as negative controls (open boxes). Each experimental point represents the mean±the SD of results obtained from three separate chambers. Fusion proteins were compared statistically with their respective negative controls.

FIG. 4A–B shows that the M ectodomains from apoptosis-inducing flaviviruses have proapoptotic properties. HeLa cells were transfected with constructs encoding $C^{95-114}$-EGFP (control, open box), $C^{95-114}$-EGFP-$M^{1-40/DEN-1}$ (DEN-1), $C^{95-114}$-EGFP-$M^{1-40/DEN-2}$ (DEN-2), $C^{95-114}$-EGFP-$M^{1-40/DEN-3}$ (DEN-3) $C^{95-114}$-EGFP-$M^{1-40/DEN-4}$ (DEN-4), $C^{95-114}$-EGFP-$M^{1-40/JE}$ (JE), $C^{95-114}$-EGFP-$M^{1-40/WN}$ (WN), or $C^{95-114}$-EGFP-$M^{1-40/YF.wt}$ (YF) (A), or with plasmids encoding $C^{95-114}$-EGFP (control; open box), $C^{95-114}$-EGFP-$M^{1-40/YF.wt}$ ($M^{1-40/YF.wt}$) or $C^{95-114}$-EGFP-$M^{1-40/YF.17D}$ ($M^{1-40/YF.17D}$) (B). Transfected HeLa cells were stained with Hoechst 33258 after 25 hours of transfection and examined for changes in nuclear morphology. The percentages of fusion protein-expressing cells displaying chromatin condensation are indicated. Each experimental point represents the mean±the SD of results obtained from three separate chambers. Fusion proteins were compared statistically with their respective controls.

Figure 5B:
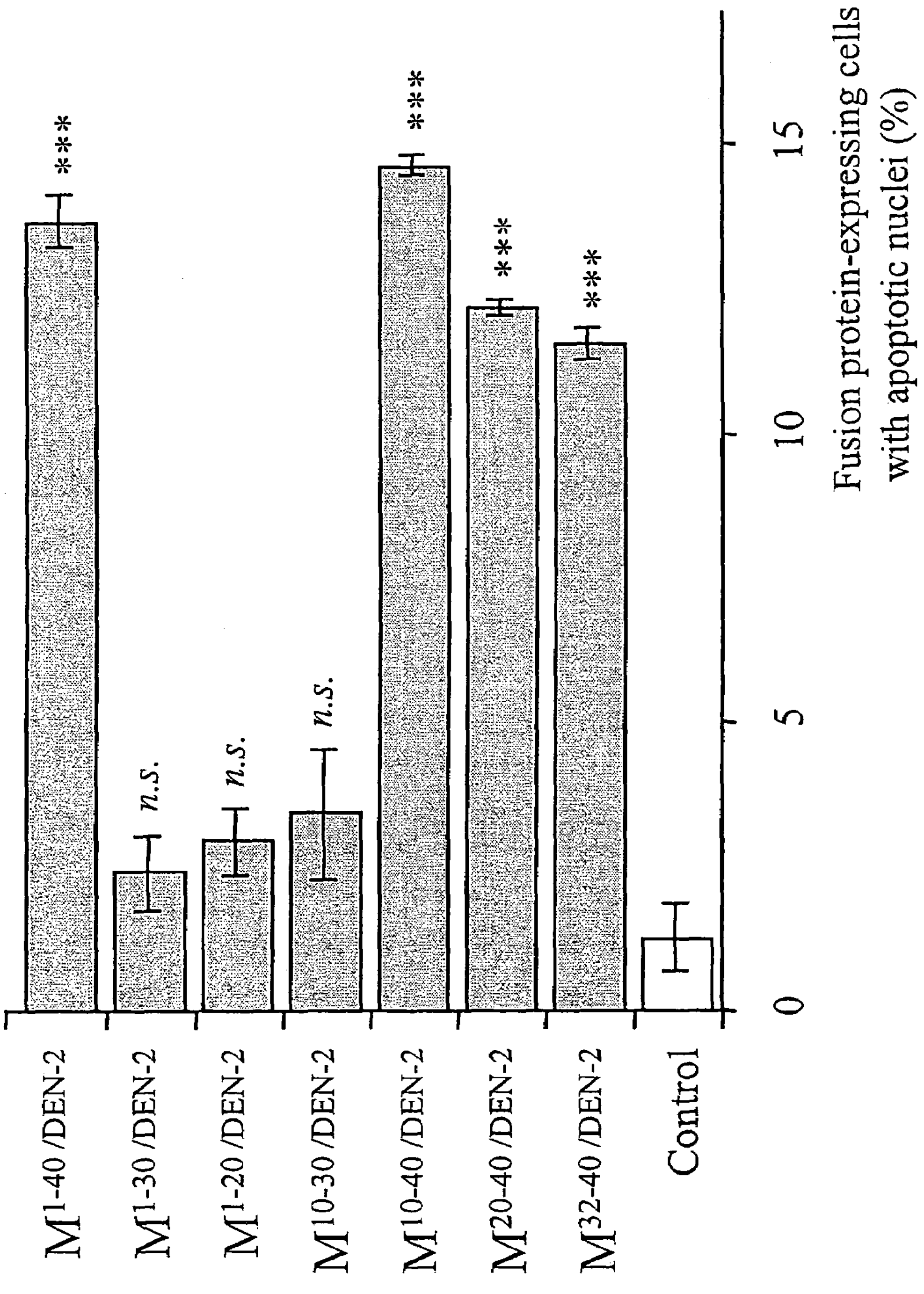
Figure 5C:
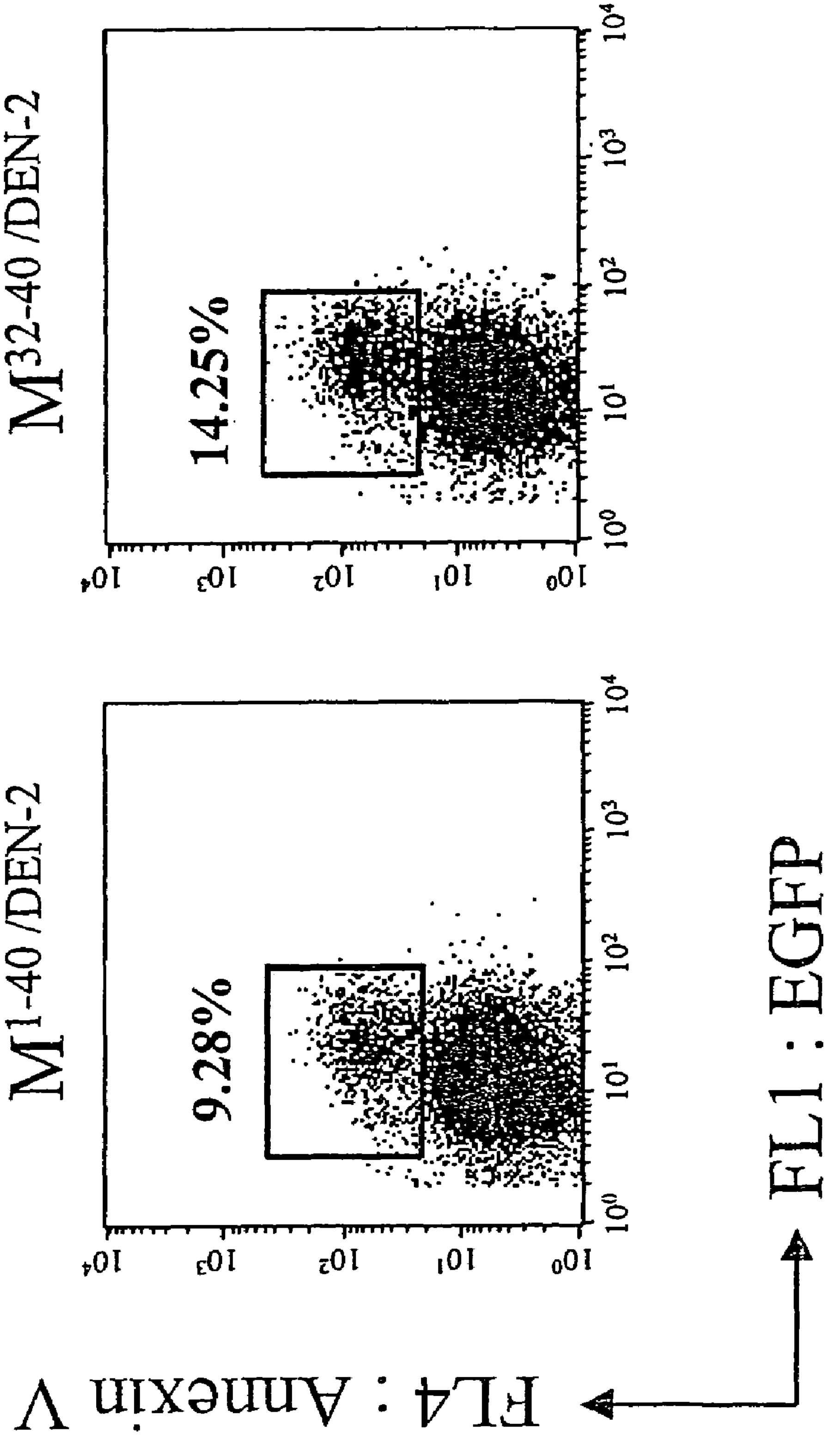

FIG. 5A–C shows that the nine carboxy-terminal amino acids of the M ectodomain constitute a proapoptotic sequence. (A) Amino acid sequence alignments for mutant proteins, (SEQ ID NOs:31–40, in descending order), the names of which are shown on the right. (B) and (C) Transfected HeLa cells were assayed for apoptotic nuclear fragmentation after 25 hours of transfection (B) or for the early stage of apoptosis after 20 hours (C). (B) HeLa cells were stained with Hoescht 33258 and examined for chromatin condensation. $C^{95-114}$-tagged EGFP (Control; open box) served as a negative control. The percentages of fusion protein-expressing cells with apoptotic nuclei are indicated. Each experimental point represents the mean±the SD of results obtained from three separate chambers. Statistical analysis for fusion proteins were carried out by comparison with the control. (C). The rate of early apoptosis was analyzed by Annexin V binding, as assessed by flow cytometry analysis. Apoptosis in fusion protein-expressing HeLa cells was defined as EGFP-positive cells that bound Annexin V-APC but excluded PI. For each sample, data from 10,000 EGFP-positive cells were collected. The percentages of $M^{1-40}$- and $M^{32-40}$-expressing cells labeled with Annexin V are indicated (square).

Figure 6:
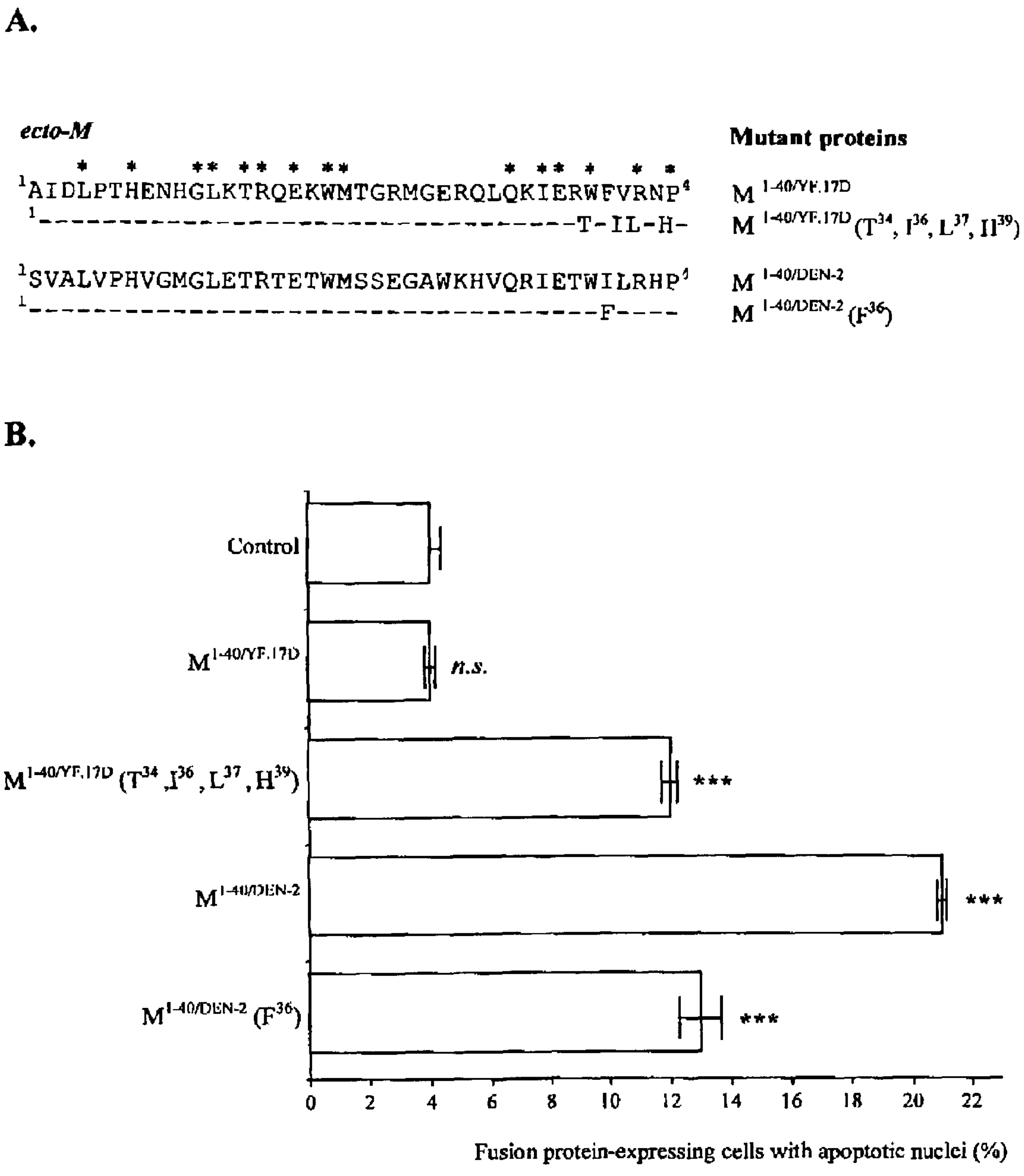

FIG. 6A–B shows that the residues M-34 to M-39 contribute to the death-promoting activity of the M ectodomain. (A) Amino acid sequence alignments of $M^{1-40/DEN-2}$ (SEQ ID NO: 31), $M^{1-40/YF.17D}$ (SEQ ID NO:37) and mutants $M^{1-40/DEN-2}$ ($F^{36}$) and $M^{1-40/YF.17D}$ ($T^{34}$, $I^{36}$, $L^{37}$, $H^{39}$). Identical amino acids are indicated (asterisks). The amino acid substitutions are underlined and indicated in bold. (B) After 25 hours of transfection, fusion protein-expressing HeLa cells were stained with Hoechst 33258 and examined for chromatin condensation. The percentages of fusion protein-expressing cells with apoptotic nuclei are indicated. Each experimental point represents the mean±the SD of results obtained from three separate chambers. Fusion proteins were compared statistically with $C^{95-114}$-tagged EGFP (Control; open box).

Figure 7:
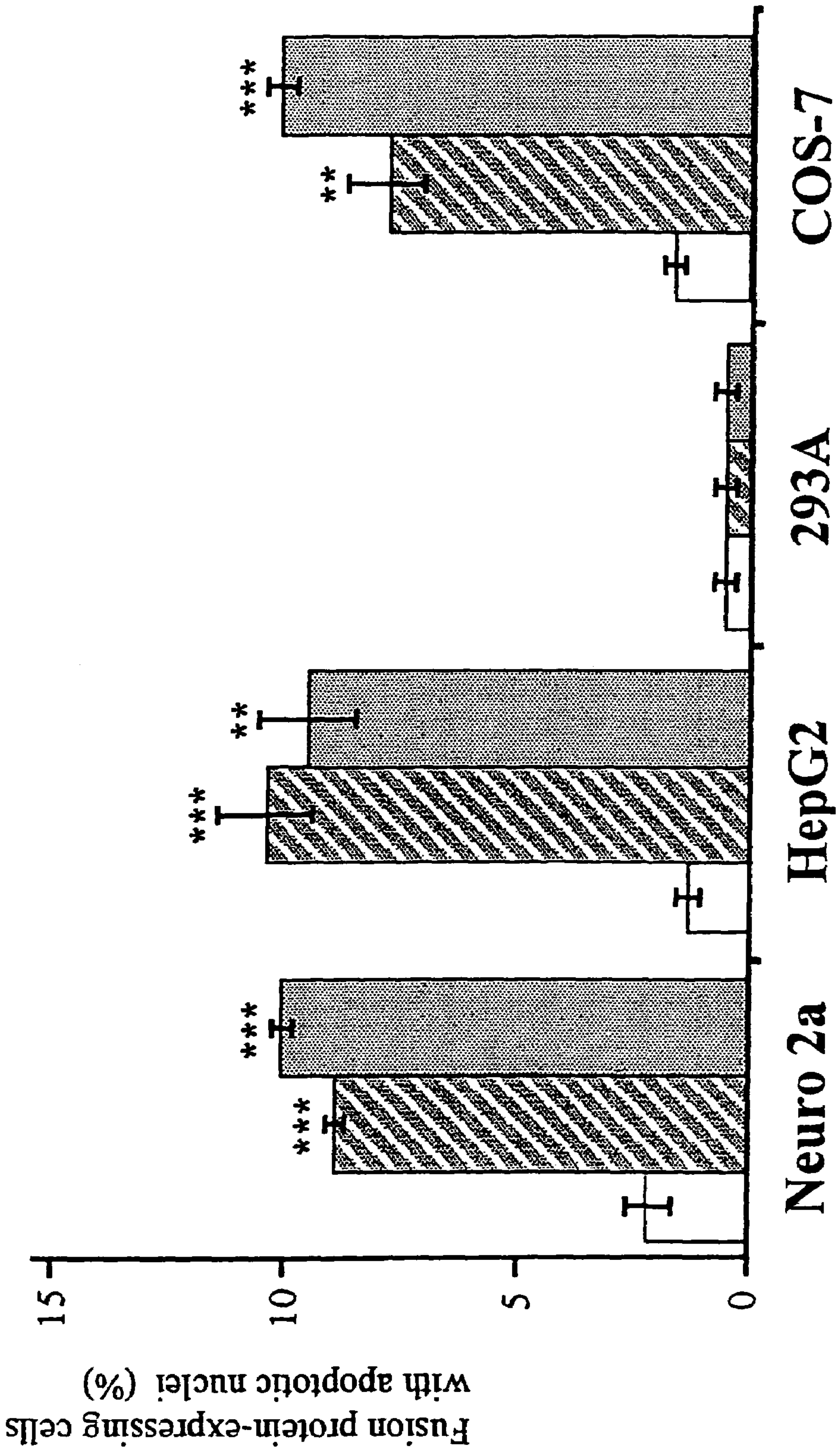

FIG. 7 shows that DEN M ectodomain induces apoptosis in cells of various origins. Tumoral Neuro 2a and HepG2 cell lines and transformed 293A and COS-7 cell lines were transfected with plasmids encoding $C^{95-114}$-EGFP-$M^{1-40/DEN-1}$ (hatched box) or $C^{95-114}$-EGFP-$M^{1-40/DEN-2}$ (filled box). Transfected cells were stained with Hoechst 33258 and examined for chromatin condensation. The percentages of fusion protein-expressing cells with apoptotic nuclei after 30 hours of transfection are indicated. Each experimental point represents the mean±the SD of results obtained from three separate chambers. Fusion proteins were compared statistically with $C^{95-114}$-tagged EGFP (open box).

Figure 8:
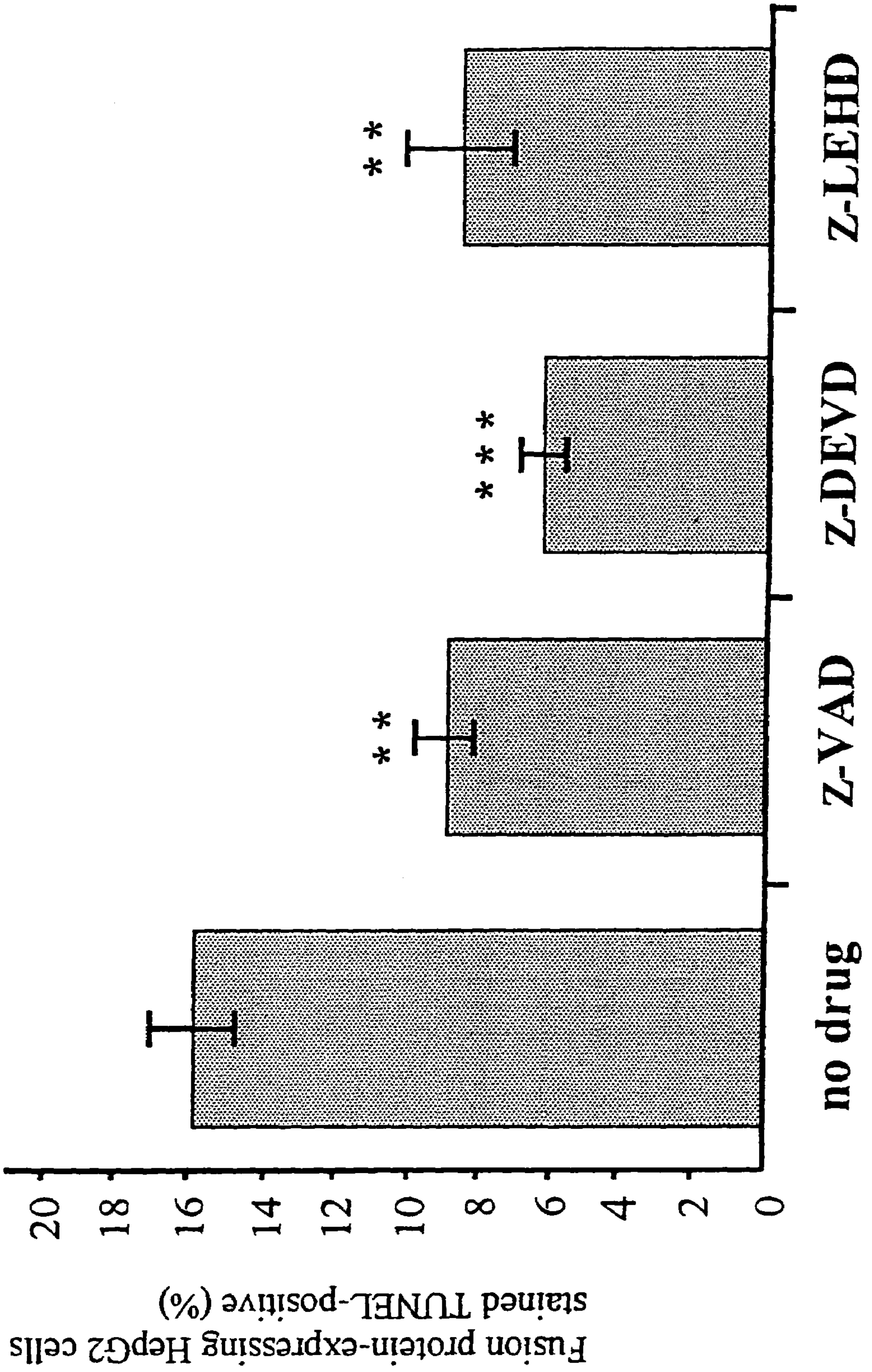

FIG. 8 shows that caspase inhibitors afford protection against the proapoptotic effects of the M ectodomain. HepG2 cells were transfected with plasmid encoding $C^{95-114}$-EGFP-$M^{1-40/DEN-2}$. During transfection, cell cultures were mock-treated (no drug) or treated with 10 μM general caspase inhibitor Z-VAD-FMK (z-VAD), 50 μM caspase-3 inhibitor Z-DVED-FMK (z-DVED), or 50 μM caspase-9 inhibitor Z-LEHD-FMK (z-LEHD). After 30 hours of transfection, the transfected cells were subjected to the TUNEL assay, as described in the legend to FIG. 2. Each experimental point represents the mean±the SD of results obtained from three separate chambers. Caspase-treated cells were compared statistically with mock-treated cells.

Figure 9B:
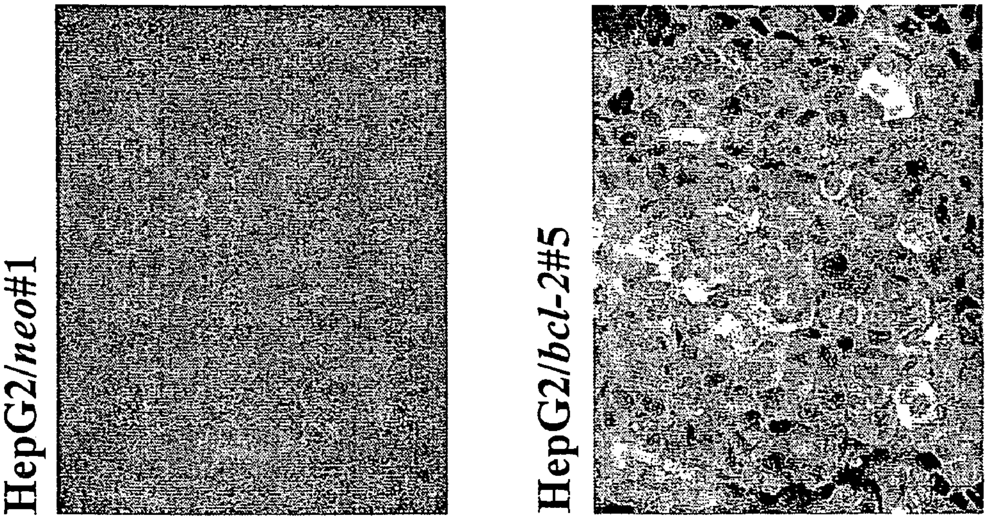
Figure 9A:
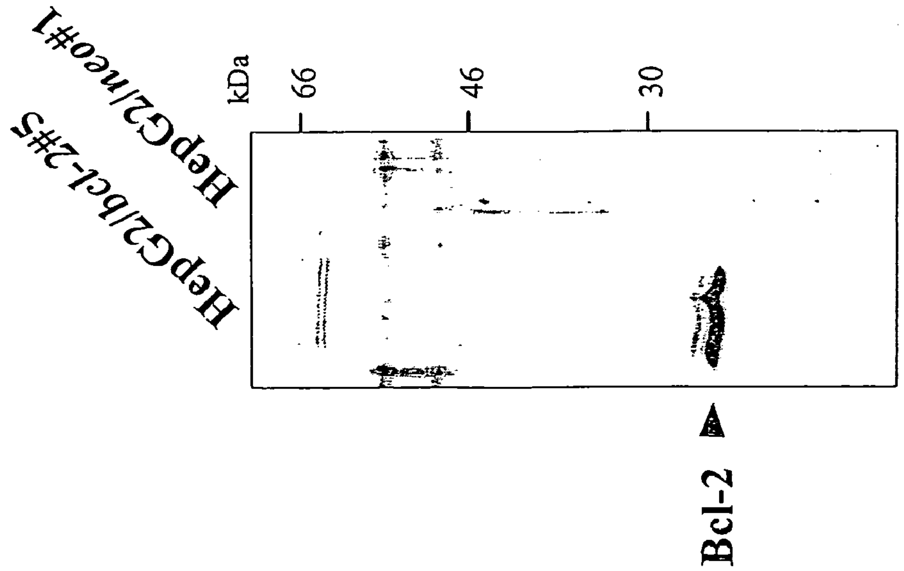
Figure 9C:
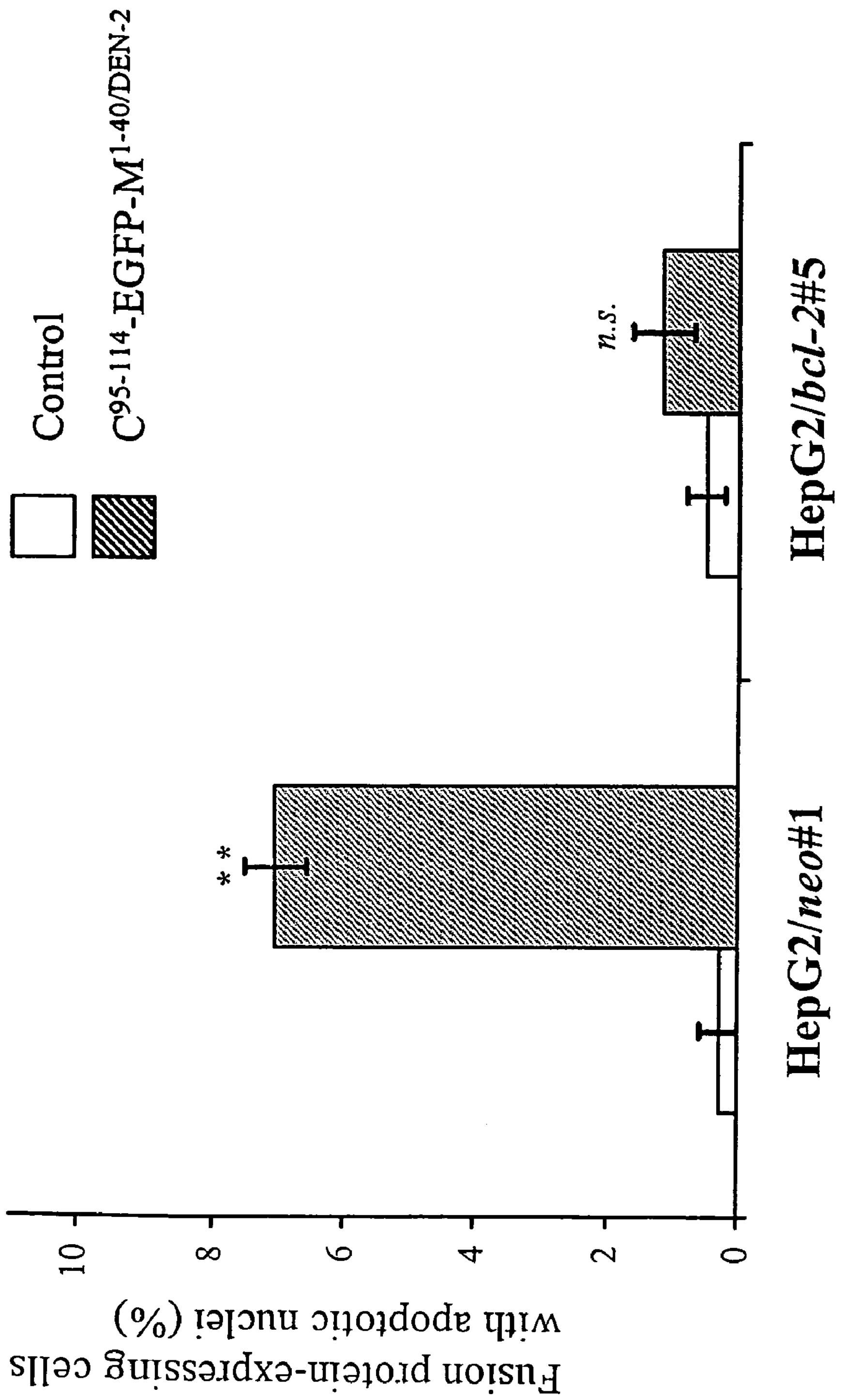

FIG. 9A–C shows that the overproduction of bcl-2 protects HepG2 cells against the proapoptotic effects of the DEN-2 M ectodomain. The overproduction of bcl-2 in HepG2 cell clones was assessed by Western blotting (A) and indirect immunofluorescence (B) assays, using antibodies specific for the human Bcl-2 protein. (C) HepG2/bcl-2#5 and HepG2/neo#1 cells were transfected with plasmids encoding $C^{95-114}$-EGFP (Control, open box) or $C^{95-114}$-EGFP-$M^{1-40/DEN-2}$ (hatched box). After 30 hours of transfection, transiently transfected cells were stained with Hoechst 33258 and examined for chromatin condensation. The percentages of fusion protein-expressing cells with apoptotic nuclei are indicated. Each experimental point represents the mean±the SD of results obtained from three separate chambers. Fusion protein was compared statistically with $C^{95-114}$-tagged EGFP.

FIG. 10 illustrates the alignment of the 40 C-terminal amino acids of M protein (M ectodomain; (SEQ ID NO:38) from 4 serotypes of the dengue virus (DEN-1 to DEN-4), attenuated virus YFV 17D, West-Nile virus (WNV) and Japanese encephalitis virus (JEV), and also specifically the alignment of the nine amino acids of the M ectodomain (SEQ ID NOs:39 and 40) from the same flavivirus which confer apoptotic activity.

FIG. 11A–D shows that peptide $M^{32-40}$ has proapoptotic activity. HeLa cells were mock-transfected (Control) or transfected with plasmid encoding EGFP$^{ER}$ or EGFP$^{ER}$-M$^{32-40}$ as described in the Materials and Methods. (A) Schematic representation of fusion constructs EGFP$^{ER}$ and EGFP$^{ER}$-M$^{32-40}$. SP, signal peptide. The fusion proteins are not drawn to scale. (B) Immunoblot assay of whole-cell lysates using a rabbit antiserum raised against EGFP (BD Clontech). (C) Apoptotic DNA degradation in transfected cells as assessed by TUNEL method. (D) Early apoptosis was defined as EGFP-expressing cells that bound Annexin V-APC but excluded PI as determined by flow cytometry. For each sample, data from 10,000 EGFP-expressing cells were collected. Each experimental point represents the mean±the standard deviations (SD) of results obtained from three separate experiments.

FIG. 12A–D shows that M$^{32-40}$ leads to disruption of mitochondrial transmembrane potential and caspase activation. HeLa cells were transfected 20 h (A, B and D) or 25 h (C) with plasmid expressing EGFP$^{ER}$ or EGFP$^{ER}$-M$^{32-40}$. (A) Flow cytometry analysis of transfected cells mock-treated (dotted line) or incubated with the mitochondrial potential sensor CMXRos (continuous line). The percentage of EGFP-expressing cells with a low $\Delta\Psi_m$ is indicated. Data from 10,000 EGFP-expressing cells were collected for each graph. A representative result of three independent experiments is shown. (B) ROS production was assessed by staining transfected HeLa cells with the ROS-sensitive dye HE. Data from 10,000 EGFP-expressing cells were collected for each graph. (C) M$^{32-40}$-expressing cells were mock-treated (Control) or treated with 50 μM general caspase inhibitor z-VAD-fmk (zVAD), 50 μM caspase-3 inhibitor z-DEVD-fmk (zDEVD), or 50 μM caspase-9 inhibitor z-LEHD-fmk (zLEHD). Caspase inhibitors were purchased from R&D systems. Apoptotic DNA degradation was observed as described in the legend to FIG. 1C. Each experimental point represents the mean±SD of results obtained from three independent cell chambers. Caspase inhibitor-treated cells were compared statistically with mock-treated cells: not significant (n.s., P>0.05) or significant (*** P<0.001), according to Fisher and Yates's t tests. (D) Immunoblot assay of whole-cell lysates using anti-PARP mAb C$_{2-10}$ (R&D systems). The PARP (116 kDa) and the caspase cleaved product (85 kDa) are shown. HeLa cells incubated 6 h with 1 μM staurosporine were used as a positive control.

Figure 13:
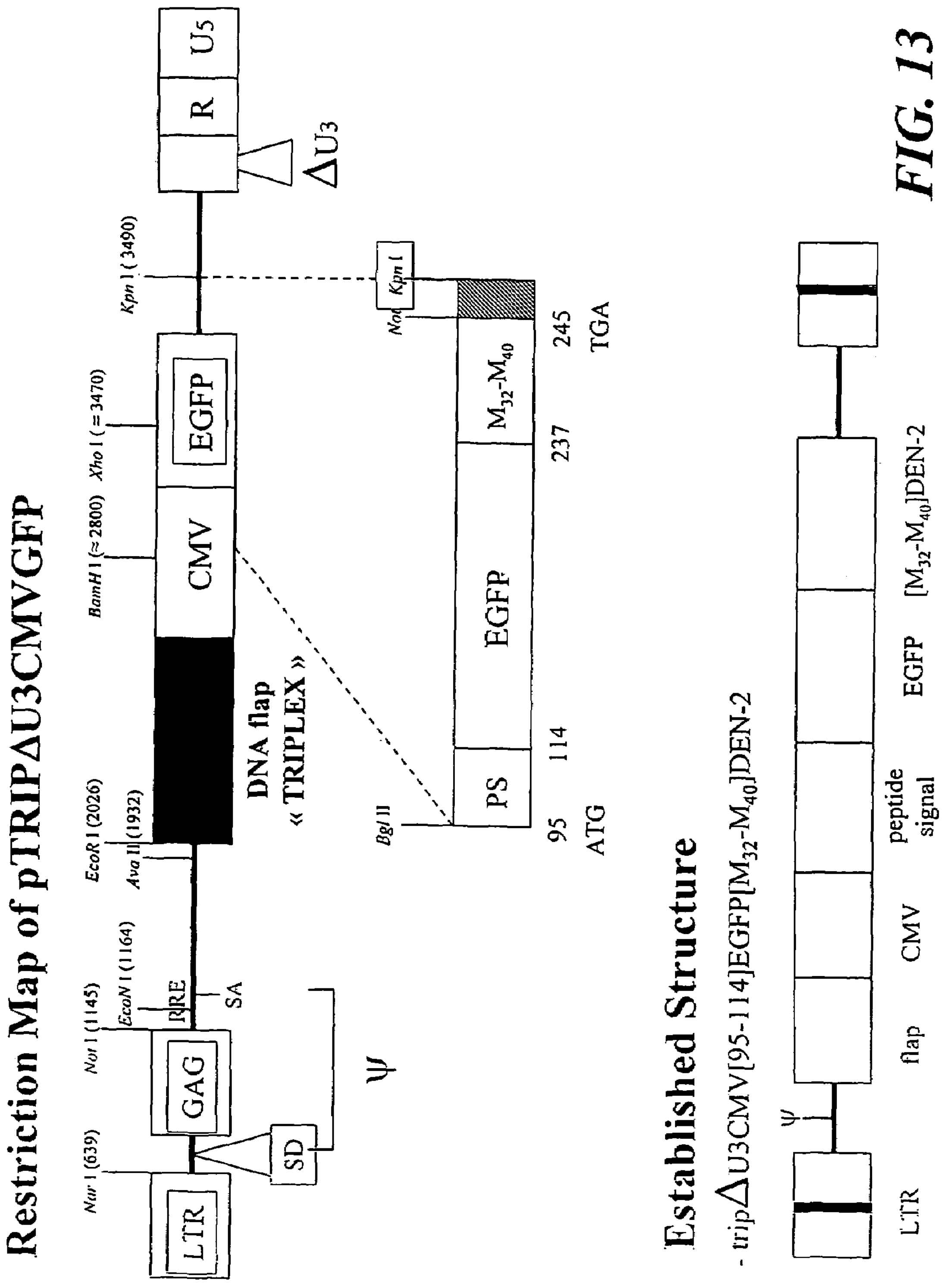

FIG. 13 represents the restriction card of plasmid Trip ΔU3 CMV[95-114] EGFP[M$_{32}$–M$_{40}$] DEN-2.

EXAMPLE 1

Expression of the M Ectodomain Leads to Apoptosis

1) Materials and Methods 1.1) Materials

Cell Lines and Viruses

The human epithelial HeLa cell line was cultured in DMEM supplemented with 10% fetal calf serum (FCS) and 2 mM L-glutamine.

The South-American strain of DEN-1 virus FGA/89 has the GenBank accession number: AF226687.

Plasmids

Viral RNA was extracted from purified flavivirus or infected cell lysates using the RNA plus reagent (Quantum Bioprobe). The RNA was reverse-transcribed using the Titan One-Step RT-PCR kit (Roche Molecular Biochemicals) according to the manufacturer's instructions. All constructs were verified by automated sequencing.

The BR/90 cDNA encoding residues C-95 to C-114 (amino acid residues are numbered as for DEN-1 virus [11]) was introduced into NheI/SmaI-digested pEGFP-N1 (this plasmid pEGFP-N1 was purchased from BD Clontech BioSciences), the eukaryotic expression vector containing the gene encoding the enhanced green fluorescent protein (EGFP). The resulting plasmid, pC$^{95-114}$-EGFP, encodes the prM translocation signal followed by six vector-specified residues, EPPVAT, fused in-frame with the N-terminus of EGFP.

Synthetic oligonucleotide primers containing recognition sites for BsrGI (5' primer) and NotI (3' primer), were used to amplify specific sequences of the flavivirus genome encoding the full-length M (residues M-1 to M-74) (see Table I below).

TABLE 1

| M | 5' primer | 3' primer | Strain |
|---|---|---|---|
| DEN-1 | 5'-gacaaacgttccgtggctctgtgacacacgtgggacttggtctag-3'<br>(SEQ ID NO:1) | 5'-ctattcccagcggccgctaggccattgatggtg-3'<br>(SEQ ID NO:2) | FGA/89 |
| DEN-2 | 5'-cacagaagactgtacagatcagtggcactcgttcc-3'<br>(SEQ ID NO:3) | 5'-atattcctagcggccgctatgtcattgaaggagcg-3'<br>(SEQ ID NO:4) | Jamaica |
| DEN-3 | 5'-agacgcgtgtacagatcagtggcgttagctccccatgtcgcc-3'<br>(SEQ ID NO:5) | 5'-gtttccgcggccgccacatcttcatgtcataggtggggtaacc-3'<br>(SEQ ID NO:6) | H-87 |
| DEN-4 | 5'-agacgagtgtacagctcagtagctttaacaccacattcgg-3'<br>(SEQ ID NO:7) | 5'-tgtttccgcggccgccgcatcgtcatccgtaggatggggcga-3'<br>(SEQ ID NO:8) | H-241 |
| JE | 5'-aagcgaatgtacagatccgtgtcggtccaaacacatggggagag-3'<br>(SEQ ID NO:9) | 5'-attgccgcggccgcgacaatttcaactgtaagccggagcgacc-3'<br>(SEQ ID NO:10) | Nakayama |
| WN | 5'-agacgcatgtacaggtcactgacagtgcag-3'<br>(SEQ ID NO:11) | 5'-cattccgcggccgctctagctgtaagctgg-3'<br>(SEQ ID NO:12) | IS-98-ST1 |

TABLE 1-continued

| | | | |
|---|---|---|---|
| YF | 5'-aggaggttgtacagggccattgacttgcctacgc atgaaaacc-3' (SEQ ID NO:13) | 5'-tgtcagtgcggccgctgcagtgtcatgagta ggccggaccaac-3' (SEQ ID NO:14) | 17D-204 |
| Mutants | 5' primer | 3' primer | Plasmid[(1)] |
| $M^{1-30/DEN-2}$ | 5'-ttttggcagtacatcaatgggcg-3' (SEQ ID NO:15) | 5'-aagatcgcggccgcaattcactggacatgtttcca ggc-3' (SEQ ID NO:16) | $M^{1-40/DEN-2}$ |
| $M^{1-20/DEN-2}$ | 5'-ttttggcagtacatcaatgggcg-3' (SEQ ID NO:15) | 5'-tttccgcggccgctctgatcacatccatgtttcag ttcag-3' (SEQ ID NO:17) | $M^{1-40/DEN-2}$ |
| $M^{9-30/DEN-2}$ | 5'-ttttggcagtacatcaatgggcg-3' (SEQ ID NO:15) | 5'-aagatcgcggccgcaattcactggacatgtttcca ggc-3' (SEQ ID NO:16) | $M^{9-40/DEN-2}$ |
| $M^{9-40/DEN-2}$ | 5'-tggttctgtacatgggaatgggactggagac acg-3' (SEQ ID NO:18) | 5'-tcttgcagttcattcagggcaccg-3' (SEQ ID NO:19) | $M^{1-40/DEN-2}$ |
| $M^{20-40/DEN-2}$ | 5'-actgaaatgtacatgtcatcagaaggggcct gg-3' (SEQ ID NO:20) | 5'-tcttgcagttcattcagggcaccg-3' (SEQ ID NO:19) | $M^{1-40/DEN-2}$ |
| $M^{32-40/DEN-2}$ | 5'-atgtcctgtacattgaaacttggatcttga g-3' (SEQ ID NO:21) | 5'-tcttgcagttcattcagggcaccg-3' (SEQ ID NO:19) | $M^{1-40/DEN-2}$ |

(1)$pC^{95-114}$-EGFP-$M^{1-40/DEN-2}$ or $pC^{95-114}$-EGFP-$M^{9-40/DEN-2}$

Plasmid $pC^{95-114}$-EGFP-$M^{1-74}$ was constructed by digesting the RT-PCR products with BsrGI and NotI and by introducing the resulting fragment into BsrGI/NotI-digested $pC^{95-114}$-EGFP, such that the full-length M was directly fused in-frame with the carboxy-terminal end of EGFP. Plasmid $pC^{95-114}$-EGFP-$M^{1-40}$ was constructed by amplifying flavivirus cDNAs encoding the M ectodomain (residues M-1 to M-40) by PCR using $pC^{95-114}$-EGFP-$M^{1-74}$ as a template and a set of 3' primers containing a stop codon (TGA) followed by a NotI restriction site. The PCR products were introduced into $pC^{95-114}$-EGFP, such that the flavivirus M ectodomains were produced as fusions with EGFP.

Plasmid Trip Δ U3 CMV[95-114] EGFP[$M_{32}$–$M_{40}$] DEN-2 derives from plasmid Trip Δ U3 CMV GFP (Zennou et al., *Cell,* 2000, 196, 173–185) (CNCM n$^0$ I-2330). Said plasmid contains upstream gene EGFP, the cDNA of virus DEN-1 BR/90 encoding amino acids 95-114 of the dengue polyprotein and downstream said EGFP gene, cDNA of DEN-2 Jamaïca virus encoding amino acids 237–245 of said polyprotein as it emerges from FIG. 13. Transfer vectors able to form triplex structures are more specifically described in the Institut Pasteur International PCT Application WO 99/55892.

To construct a series of mutants with deletions in the DEN-2 M ectodomain ($M^{1-40/DEN-2}$), PCR fragments were generated using $pC^{95-114}$-EGFP-$M^{1-40/DEN-2}$ or $pC^{95-114}$-EGFP-$M^{9-40/DEN-2}$ as a template and primers containing recognition sites for BsrGI and NotI and a stop codon TGA (see Table I). The PCR products encoding mutant proteins were inserted into $pC^{95-114}$-EGFP downstream from the EGFP gene.

1.2) Method

Transient Transfection of Cells

Cells were distributed to Permanox Lab-tek chambers (Nalge Nunc International) or 6-well plates. After one day of culture, cell monolayers were transfected with 6 μg of plasmid per $10^6$ cells in the presence of FuGene 6 transfection reagent (Roche Molecular Biochemicals), according to the manufacturer's instructions. The fusion proteins were detected by monitoring the autofluorescence of EGFP.

In Situ Detection of Apoptotic Cells

The cells were fixed by incubation with 3.2% paraformaldehyde (PFA) in PBS for 20 min. The Inventors have investigated the nuclear changes associated with apoptotic cell death by incubating fixed cells with 0.1 μg/ml Hoechst 33258 (Sigma) in 0.1% citrate buffer (pH 6.0) for 10 min at room temperature. Cells were considered to be apoptotic if their nuclei displayed margins and chromatin condensation. At least 200 transfected cells from three independent cell chambers were used to quantify apoptosis. Apoptosis-induced DNA breaks were detected by the deoxyterminal transferase-mediated dUTP nick-end labeling (TUNEL) method as previously described (11). Nuclear TUNEL assay was performed with CY™ 3 conjugated-streptavidin (Jackson Immunoresearch). Cells were examined under an AXIOPLAN 2 fluorescence microscope (Zeiss). Images were processed on a computer, using RS Image 1.07, SimplePCI 5.1, Adobe Photoshop and Powerpoint software.

2) Results

The inventors have shown that the infection of host cells with DEN-1 virus isolate FGA/89 leads to apoptosis (12–14). They investigated the role of DEN-1 envelope glycoproteins in the induction of apoptosis by examining the stable cell line N2aprM+E which carries the FGA/89 cDNA encoding prM plus E under the control of an inducible exogenous promoter (7). Apoptosis was observed in induced N2aprM+E cells, suggesting that prM and E are involved in DEN virus-induced apoptosis.

The inventors have investigated whether the anchor regions of DEN envelope glycoproteins were involved in apoptosis induction. The FGA/89 cDNAs encoding the carboxy-terminal regions of prM and E were inserted into a mammalian expression vector under the control of the human cytomegalovirus IE promoter. EGFP-tagged DEN proteins were constructed by fusing viral gene sequences immediately downstream from the reporter gene encoding EGFP (FIG. 1).

As the carboxy-terminal part of prM contains M, the EGFP-tagged M proteins contained either the complete M protein, including the TMDs (residues M-1 to M-74), or only the M ectodomain (residues M-1 to M-40) (FIG. 1). The EGFP-tagged E proteins included either the stem alone (residues E-392 to E-439) or the stem-anchor region (residues E-392 to E-487) of the E protein (FIG. 1). The sequence encoding the internal signal sequence ($C^{95-114}$), which is located at the junction of the DEN-1 C and prM proteins and directs the translocation of prM into the lumen of the ER (5, 41), was inserted upstream from sequences encoding the EGFP-tagged DEN proteins (FIG. 1).

The Inventors assessed the production of the chimeric proteins by transient transfection of HeLa cells. After 15 hours of transfection, transiently-transfected HeLa cells were assayed for EGFP production by direct fluorescence analysis. Upon transfection with pEGFP-N1, autofluorescence of EGFP was observed in more than 50% of the HeLa cells. Western blot assays with anti-EGFP antibodies showed that the electrophoretic mobility of EGFP in $C^{95-114}$-EGFP-expressing HeLa cells was similar to that of the EGFP encoded by the control plasmid, pEGFP-N1. This demonstrates that proteolytic cleavage occurred at the junction between the prM translocation signal and EGFP.

The Inventors have evaluated the ability of EGFP-tagged DEN proteins to induce apoptosis by means of transient transfection experiments with HeLa cells. Surprinsingly, they found that the production of $C^{95-114}$-EGFP-$M^{1-40/DEN-1}$, which includes the M ectodomain, resulted in cell death (FIG. 2A). Approximately 15% of $M^{1-40/DEN-1}$-expressing HeLa cells displayed chromatin condensation after 25 hours of transfection, with a peak of 20% at 30 hours, as assessed by Hoechst 33258 staining (FIG. 2B). To confirm that apoptosis occurred in HeLa cells producing $C^{95-114}$-EGFP-$M^{1-40/DEN-1}$, apoptotic DNA fragmentation was assessed by the nuclear TUNEL assay (25). The Inventors observed apoptotic nuclear fragmentation in more than 15% of $M^{1-40/DEN-1}$-expressing cells after 25 hours of transfection (FIG. 2C). The proportion of apoptotic cells determined by the TUNEL method correlated well with that determined by counting cells with nuclei displaying apoptotic morphology. As production of the full-length M protein or the stem-anchor region of the E protein did not result in cell death (FIG. 2A), the cytotoxicity of the M ectodomain was not due to an overexpression artifact after transfection.

To exclude the possibility that EGFP contributes to the death-promoting activity of the EGFP-tagged $M^{1-40/DEN-1}$ protein, the deletion mutant protein $C^{95-114}$-$M^{6-40/DEN-1}$ consisting of residues M-6 to M-40 directly fused to the prM translocation signal (FIG. 1) was constructed. Upon transfection with p$C^{95-114}$-$M^{6-40/DEN-1}$, approximately 10% of HeLa cells displayed chromatin condensation after 25 hours of transfection. These results suggest that the M ectodomain (hereafter referred to as ecto-M) of DEN-1 virus induces apoptosis in transfected HeLa cells.

EXAMPLE 2

Induction of Apoptosis by Transport of the M Ectodomain Through the Secretory Pathway 1) Materials and Methods 1.1) Materials Cell Lines and Plasmids HeLa cell line was used as in Example 1.

The plasmid pEYFP-Golgi was purchased from BD Clontech BioSciences.

To construct pGalT$^{1-80}$-EGFP-$M^{1-40/DEN-1}$, a 0.9 kb fragment containing the entire EGFP-$M^{1-40/DEN-1}$ fragment was excised from p$C^{95-114}$-EGFP-$M^{1-40/DEN-1}$ with BamHI and NotI. This fragment was inserted into BamHI/NotI-digested pEYFP-Golgi, such that EGFP-$M^{1-40/DEN-1}$ was fused in-frame with the N-terminal region of 1,4-galactosyltransferase (GalT).

To construct pCR-CD72$^{1-136}$, total RNA from the spleens of BALB/c ByJRj mice was reverse-transcribed to generate cDNA, which was used as template for PCR. An RT-PCR fragment encoding the endodomain followed by the transmembrane domain of mouse CD72 glycoprotein (nt 1–445) was generated, fusing the following synthetic primers: 5'-TGCTGGAGGAATAGCAGTCTTAAAAATTGGC-3' (SEQ ID NO:22) corresponding to nt 1–31 of the 5' end of the CD72 cDNA and 5'-TATTGGTGGCTTCCCAAATCCTGGTCCCC-3' (SEQ ID NO:23) corresponding to nt 416–445 of the 3' end of the CD72 cDNA. The RT-PCR product was directly inserted into pCR 2.1 TOPO (TOPO TA cloning kit, Invitrogen) according to the manufacturer's instructions to give pCR-CD72$^{1-136}$.

The plasmids pCD72$^{1-118}$-EGFP-$M^{1-40/DEN-1}$ were generated by amplifying the cDNA encoding the amino-terminal region of CD72 by PCR, using pCR-CD72$^{1-136}$ as a template and the following primers: 5'-GAGGCGGCTAGCGCTATGGCTGACGCTATCACG-3' (SEQ ID NO:30) corresponding to the 5'end of the CD72 gene and extended by 11 nucleotides to include a NheI restriction site and 5'-AGACACCCGGGGATAGAGAACTCCCAGGC-3' (SEQ ID NO:24) corresponding to nt 387–402 at the 3'end of the CD72 gene and extended by 14 nucleotides to include a SmaI restriction site. The PCR product was digested with NheI and SmaI and inserted between the NheI and SmaI sites of p$C^{95-114}$-EGFP-$M^{1-40/DEN-1}$ to generate pCD72$^{1-118}$-EGFP-$M^{1-40/DEN-1}$.

To construct p$C^{95-114}$-EGFP-$M^{1-40/DEN-1}$-KDEL, pGalT$^{1-80}$-EGFP-$M^{1-40/DEN-1}$-KDEL and pCD72$^{1-118}$-EGFP-$M^{1-40/DEN-1}$-KDEL, PCR fragments containing the DEN-1 M ectodomain ($M^{1-40/DEN-1}$) followed by the KDEL motif were generated with the 3' primer

```
                                        (SEQ ID NO:25)
5'-TAAAGCGGCCGCTCACAACTCGTCTTTTGGGTGTCTCAAAGCCCAA

GTCTCCAC-3'
```

corresponding to the KDEL sequence and extended by 12 nucleotides to include a stop codon (TGA) followed by a NotI restriction site.

1.2) Methods

The methods of Example 1 were used.

2) Results

The death-promoting activity of the EGFP-tagged M ectodomain was abolished if the prM translocation sequence was deleted (FIG. 2A), suggesting that the transport of ecto-M through the secretory pathway plays a key role in the initiation of apoptosis.

The Inventors investigated whether the presence of EGFP-tagged $M^{1-40/DEN-1}$ in the ER was sufficient to trigger apoptosis by assessing the cytotoxicity of the mutant protein $C^{95-114}$-EGFP-$M^{1-40/DEN-1}$-KDEL,consisting of the ER retrieval KDEL sequence fused to the carboxy-terminal end of the DEN-1 M ectodomain. The KDEL motif is present in several luminal ER proteins and is recognized by a specific receptor that mediates retrograde transport between the Golgi apparatus and the ER (38). Upon production of $C^{95-114}$-EGFP-$M^{1-40/DEN-1}$-KDEL,the autofluorescence of EGFP was readily detected in the ER of transfected HeLa cells, indicating that the ER retrieval sequence promotes the retention of $M^{1-40/DEN-1}$ within the ER (FIG. 3A). The production of $C^{95-114}$-EGFP-$M^{1-40/DEN-1}$-KDEL caused no cytopathic effects (CPEs) (FIG. 3B), indicating that the ER retrieval sequence may prevent ecto-M-mediated cell death. This finding is consistent with the observation that the presence of the anchor region ($C^{95-114}$-EGFP-$M^{1-74}$ fusion protein) abolished the death-promoting activity of the M ectodomain (FIG. 2A), possibly by favoring its retention in the ER compartment (6).

To investigate whether the Golgi localization of ectoM is required for the induction of apoptosis, $GalT^{1-80}$-EGFP-$M^{1-40/DEN-1}$ and $GalT^{1-80}$-EGFP-$M^{1-40/DEN-1}$-KDEL fusion proteins containing the amino-terminal region of human beta 1,4-GalT were constructed. This region of 1,4-GalT contains the membrane-anchoring signal peptide that targets the protein to the trans-medial region of the Golgi apparatus (19). Upon production of $GalT^{1-80}$-EGFP-$M^{1-40/DEN-1}$, the autofluorescence of EGFP was readily detected in the Golgi apparatus of transfected HeLa cells (FIG. 3A). As observed by confocal microscopy, trans-Golgi-located $\alpha$-mannosidase II and $GalT^{1-80}$-EGFP-$M^{1-40/DEN-1}$ were colocalized in the same Golgi subcompartment. Unlike $C^{95-114}$-EGFP-$M^{1-40/DEN-1}$, neither $GalT^{1-80}$-EGFP-$M^{1-40/DEN-1}$ nor $GalT^{1-80}$-EGFP-$M^{1-40/DEN-1}$-KDEL caused CPEs. (FIG. 3B).

Thus, the studies of the present invention at this point suggested that the exit of ecto-M from the Golgi apparatus was required for the induction apoptosis. To investigate this issue, a fusion protein, $CD72^{1-118}$-EGFP-$M^{1-40/DEN-1}$, containing the cytosolic tail of a type II integral membrane glycoprotein, CD72 (52) was engineered, in place of the ER targeting signal of prM. Residues $CD72^{1}$ to $CD72^{118}$ encompass the membrane-anchoring signal peptide that targets the glycoprotein to the plasma membrane (PM). The PM, and to a lesser extent the Golgi apparatus, was clearly labelled in transfected HeLa cells producing $CD72^{1-118}$-EGFP, indicating that the CD72 translocation signal mediates the engagement of a transport pathway at the cell surface. Both the Golgi apparatus and the cell surface were clearly labeled in HeLa cells producing $CD72^{1-118}$-EGFP-$M^{1-40/DEN-1}$, whereas only the ER was stained in HeLa cells producing $CD72^{1-118}$-EGFP-$M^{1-40/DEN-1}$-KDEL (FIG. 3A). Upon transfection with p$CD72^{1-118}$-EGFP-$M^{1-40/DEN-1}$, apoptotic nuclear fragmentation was observed in more than 15% of fusion protein-expressing HeLa cells after 30 hours of transfection (FIG. 3B). In contrast, production of $CD72^{1-118}$-EGFP or $CD72^{1-118}$-EGFP-$M^{1-40/DEN-1}$-KDEL did not result in cell death. Taken together, these results suggest that the export of ecto-M from the Golgi apparatus to the plasma membrane is essential for the initiation of apoptosis. Replacement of the prM translocation sequence by the CD72 membrane-anchoring signal peptide preserved the death-mediating activity of EGFP-tagged $M^{1-40/DEN-1}$ (FIG. 3B). Thus, ecto-M may exert its cytotoxic effects by activating an apoptotic signaling pathway that does not require a soluble form.

EXAMPLE 3

Proapoptotic Properties of the M Ectodomains of JE, WN, and YF Viruses

1) Materials and Methods 1.1) Materials

Viruses

The DEN-1 virus strains FGA/89 and BR/90, the DEN-2 virus strain Jamaica (GenBank accession number: M20558), the DEN-3 virus strain H-87 (GenBank accession number: NC 001475), the DEN-4 virus strain H-241 (GenBank accession number: NC 002640), the JE virus strain Nakayama (JE virus strain SA[V], GenBank accession number: D90194), and the WN virus strain IS-98-ST1 (GenBank accession number: AF481864) were produced in cultured Aedes pseudocutillaris AP61 mosquito cells, as previously described (11). The YF virus strain 17D-204 Pasteur (GenBank accession number: X15062) was produced in human SW13 cells (10).

Expression Vectors

Mutant protein $C^{95-114}$-EGFP-$M^{1-40/YF.wt}$ was generated using p$C^{95-114}$-EGFP-$M^{1-40/YF.17D}$ as a template and the 3' primer 5'-AGAGTCGCGGCCGCAAATCAGGGGTTC-CTCACCAACCATCTCTC-3' (SEQ ID NO:26) extended by 20 nucleotides to include a stop codon (TGA) followed by a NotI restriction site.

1.2) Methods

The software used for sequence comparison was the program CLUSTAL W (53, 54).

2) Results

As the DEN-1 M ectodomain induced apoptosis, the Inventors have investigated whether the M ectodomains of other DEN serotypes and of other apoptosis-inducing flaviviruses, such as wild-type strains of JE, WN and YF viruses, also cause cell death. Production of the various EGFP-tagged M ectodomains was confirmed by Western blotting. All flavivirus M ectodomains induced apoptosis after 25 hours of transfection (FIG. 4A), suggesting that the proapoptotic properties of ecto-M are conserved among apoptosis-inducing flaviviruses. The M ectodomains of DEN-1 and DEN-2 viruses were the most potent inducers of apoptosis.

Comparison of the genomes of the YF vaccine strains 17D and French neurotropic virus (FNV) with the parental and other wild-type YF viruses revealed a common difference at position M-36: the leucine residue at this position in the wild-type YF viruses ($M^{1-40/YF.wt}$) was replaced by a phenylalanine ($M^{1-40/YF.17D}$) during attenuation (35). Unlike EGFP-tagged $M^{1-40/YF.wt}$, $C^{95-114}$-EGFP-$M^{1-40/YF.17D}$ did not trigger apoptosis in transfected HeLa cells (FIG. 4B). Thus, the $I^{36}F$ substitution observed in vaccine strains abolishes the death-promoting activity of the YF M ectodomain.

EXAMPLE 4

Determination of a Six-Nine Residues Sequence Required for the Induction of Apoptosis by the M Ectodomain 1) Materials and Methods 1.1) Materials Expression Vectors Mutant protein $C^{95-114}$-EGFP-$M^{1-40/YF.17D}$ ($T^{34}$, $I^{36}$, $L^{37}$, $H^{39}$) was generated using p$C^{95-114}$-EGFP-$M^{1-40/YF.17D}$ as a template and the 3' primer 5'-AGAGTCGCGGCCGCAAATCAGGGGT-GCCTCAGGATCCATGT—CTCAATCTTTTGGAGTTGCC-3' (SEQ ID NO: 27) extended by 21 nucleotides to include a stop codon (TGA) followed by a NotI restriction site.

1.2) Methods

Flow Cytometry Analysis of Early Apoptosis

Apoptotic assays were carried out by surface staining with the $Ca^{2+}$-dependent phosphatidylserine (PS)-binding protein Annexin V. Transfected HeLa cells were labeled by incubation with Annexin V-APC (BD Pharmingen BioSciences), and 5 μg/ml of propidium iodide (PI) (Sigma) in a HEPES-based buffer (140 mM NaCl, 2.5 mM $CaCl_2$, 10 mM HEPES [pH 7.4]) for 15 min on ice according to the manufacturer's instructions. The stained cells were analyzed in a FACS-Calibur (Becton-Dickinson) using CellQuest 3.3 software.

Other methods (see example 1).

2) Results

The Inventors tried to identify the amino acid residues critical for the death-promoting activity more precisely, using a series of fusion proteins consisting of EGFP fused to truncations from both ends of the 40-amino acid ectodomain of the DEN-2 M protein. The amino acid sequences of the mutant proteins are given in FIG. 5A. The apoptotic effects of the mutant proteins were assessed in HeLa cells after 25 hours of transfection. The production of truncated ecto-M mutant proteins containing only the first 30 amino acids of the DEN-2 ecto-M caused no CPEs in transfected HeLa cells (FIG. 5B). Thus, the amino-terminal part of ecto-M is not required for the induction apoptosis. The production of mutant proteins containing residues M-30 to M-40 induced apoptotic changes in nuclei (FIG. 5B), suggesting that the last amino acids are involved in the induction of apoptosis.

With a view to identifying the minimal sequence of the DEN-2 M ectodomain responsible for the induction of apoptosis, a construct encoding the 9 carboxy-terminal amino acids located at positions 32 to 40 fused to EGFP was engineered (FIG. 5A). The Inventors have investigated $M^{32\text{-}40/DEN\text{-}2}$-mediated cell death by flow cytometry, using the Annexin V affinity assay, which detects phosphatidylserine (PS) translocated to the outer layer of the cell membrane. The exposure of membrane PS is an early indicator of apoptosis. The fusion proteins $C^{95\text{-}114}$-EGFP-$M^{1\text{-}30/DEN\text{-}2}$ and $C^{95\text{-}114}$-EGFP-$M^{1\text{-}40/DEN\text{-}2}$ were used as negative and positive controls, respectively. In 3 independent experiments, the transfected HeLa cells producing $C^{95\text{-}114}$-EGFP-$M^{32\text{-}40/DEN\text{-}2}$ displayed significantly higher fraction of EGFP-positive cells labeled with Annexin V-APC that did cells producing $C^{95\text{-}114}$-EGFP-$M^{1\text{-}40/DEN\text{-}2}$ (FIG. 5C, squares). Thus, residues $^{32}$IETWALRHP$^{40}$ are responsible for the death-promoting activity of DEN-2 ecto-M. HeLa cells producing $C^{95\text{-}114}$-tagged EGFP and $C^{95\text{-}114}$-EGFP-$M^{1\text{-}30/DEN\text{-}2}$ also contained a subpopulation of Annexin V-labeled cells (FIG. 5C). It is likely that overproduction of EGFP has cytotoxic effects.

The Inventors have investigated whether the nine carboxy-terminal amino acids of the DEN-2 M ectodomain are potent in triggering apoptosis by introducing the substitutions $R^{34}$T, $L^{36}$I, $V^{37}$L and $N^{39}$H into the EGFP-tagged $M^{1\text{-}40/YF.17D}$ which had lost its cytotoxicity (FIG. 6A). The resulting mutant protein $C^{95\text{-}114}$-EGFP-$M^{1\text{-}40/YF.17D}$ ($T^{34}$, $I^{36}$, $L^{37}$, $H^{39}$) provokes apoptosis in transfected HeLa cells (FIG. 6B), narrowing down the region responsible for the death-promoting activity of DEN-2 ecto-M to residues M-34 to M-39.

The effect of the $F^{36}$ mutation on the death-promoting activity of DEN ecto-M was evaluated by generating a fusion protein, $C^{95\text{-}114}$-EGFP-$M^{1\text{-}40/DEN\text{-}2}$ ($F^{36}$), with a phenylalanine residue in position 36 of the DEN-2 M ectodomain (FIG. 6A). In transfected HeLa cells, the resulting mutant protein $C^{95\text{-}114}$-EGFP-$M^{1\text{-}40/DEN\text{-}2}$ ($F^{36}$) induced apoptosis significantly less efficiently than $M^{1\text{-}40/DEN\text{-}2}$ (FIG. 6B). The overall apoptosis-inducing activity of the M ectodomain reflected the intrinsic proapoptotic properties of residues M-32 to M-40, and the substitution of a leucine (YF ecto-M) or an isoleucine (DEN-2 ecto-M) for the phenylalanine in position M-36 can affect these properties.

EXAMPLE 5

Induction of Apoptosis in Tumor and Transformed Cells by the Den M Ectodomains 1) Materials and Methods 1.1) Materials Cell Lines Mouse neuroblastoma Neuro 2a cells were cultured as previously described (14). The human epithelial 293A cell line was purchased from Quantum Bioprobe. The monkey kidney COS-7 cell line was generously provided by F. Delebecque (Pasteur Institute). The 293A and COS-7 cell lines were cultured in DMEM supplemented with 10% fetal calf serum (FCS) and 2 mM L-glutamine.

1.2) Methods

The same methods as in previous examples were used.

2) Results

As DEN virus induces apoptosis in mouse neuroblastoma Neuro 2a and human hepatoma HepG2 cells (8, 12–14, 22, 30, 33, 44), the ability of the DEN M ectodomain to cause death was tested in these susceptible cell lines. The Inventors have shown that transfected Neuro 2a cells and HepG2 cells producing $C^{95}$-" "4-EGFP-$M^{1\text{-}40/DEN\text{-}1}$ or $C^{95\text{-}114}$-EGFP-$M^{1\text{-}40/DEN\text{-}2}$ underwent apoptosis after 30 hours of transfection (FIG. 7), suggesting that DEN ecto-M induces apoptosis in tumor cells of various origins.

Transformed fibroblasts from monkey kidney COS-7 and human embryonic kidney 293A cell lines display an anti-apoptosis activity (16, 18, 46). COS-7 cells contain an integrated copy of the complete early region of Simian Virus 40 (SV 40) DNA (18) and 293A cells express Adenovirus 5 (Ad5) early regions E1A and E1B (32). The death-promoting activity of ecto-M was assayed in both types of cell line. The transfected COS-7 cells that produced $C^{95\text{-}114}$-EGFP-$M^{1\text{-}40/DEN\text{-}1}$ or $C^{95\text{-}114}$-EGFP-$M^{1\text{-}40/DEN\text{-}2}$ underwent apoptosis after 30 hours of transfection (FIG. 7). In contrast to what was observed in COS-7 cells, the production of the EGFP-tagged ecto-M caused no CPEs in transfected 293A cells (FIG. 7). Transiently-transfected 293A cells producing $C^{95\text{-}114}$-EGFP-$M^{1\text{-}40/DEN\text{-}1}$ or $C^{95\text{-}114}$-EGFP-$M^{1\text{-}40/DEN\text{-}2}$ were still observed after 72 hours of transfection. Thus, 293A cells are protected against the death-promoting activity of DEN ecto-M.

EXAMPLE 6

Partial Inhibition of the Apoptotic Effect of the M Ectodomain by Caspase Inhibitors and Blocking of the Apoptotic Effect by Bcl-2

1) Materials and Methods 1.1) Materials

Human hepatoma HepG2 cells were cultured as previously described (14).

pZipBcl-2, which contains the sequence encoding human Bcl-2, was generously provided by J. M. Hardwick (Johns Hopkins University, Baltimore, Md.) (55).

1.2 Methods

Establishment of HepG2 Cell Clones Overproducing Bcl-2

The cDNA encoding human Bcl-2 was inserted into pCI-neo (BD Clontech Biosciences), to generate pCI-Bcl-2. Cell clones that stably produced the Bcl-2 protein were established by transfecting HepG2 cells with pCI-Bcl-2 in the presence of DOTAP liposomal transfection reagent (Roche Molecular Biochemicals), according to the manufacturer's instructions. The transfected cells were selected on medium containing G418 neomycin (France Biochem). Cell lines stably producing Bcl-2 protein were cloned from single cells by limiting dilution. Western blots were performed with rabbit antiserum directed against the human Bcl-2 protein (Santa Cruz). Indirect immunofluorescence assays were performed with mouse monoclonal antibodies specific for the human Bcl-2 protein (BD Pharmigen).

Immunoblotting Procedure

HepG2 cells were cultured in 6-well plates ($10^6$ cells/well). Cell monolayers were lysed by incubation in 0.4 ml of lysis buffer I (50 mM glucose, 10 mM EDTA, 25 mM Tris-HCl [pH 8.0]) containing a protease inhibitor cocktail for 10 min at 4° C. A solution of 0.2 ml of lysis buffer II (6 M urea, 6% β-mercapto-ethanol, 3% SDS, 0.003% bromophenol blue, 50 mM Tris-HCl [pH 6.8]) was then added and incubated the mixture at room temperature for 1 h. For western blotting, cell lysates were heated for 15 min at 65° C., subjected to SDS-PAGE in a 15% gel acrylamide gel and then transferred onto a PVDF membrane (Roche Molecular Biochemicals). The membranes were washed in TBS (150 mM NaCl, 50 mM Tris-HCl [pH 7.5]) and then blocked in blocking buffer (3% nonfat milk powder, 2% FCS, 1/2000 Triton X-100 in TBS) for 30 min. Membranes were probed with the primary antibody in blocking buffer overnight at 4° C. Primary antibody binding was detected by incubation with a secondary antibody, goat anti-rabbit-AP (alkaline phosphatase-coupled antibody) (BioSys). NBT/BCIP reagents were used to detect bound secondary antibodies.

2) Results

The Inventors have investigated the cellular apoptotic pathway activated by the M ectodomain.

It has been suggested that Bcl-2 regulates apoptosis by preventing the activation of caspases (1, 51). The Inventors have investigated whether the overexpression of bcl-2 protected HepG2 cells against the apoptotic effects of $M^{1-40/DEN-2}$ by establishing permanent HepG2 cell lines that stably overexpressed human Bcl-2, by transfection with pCI-Bcl-2. Western blot analysis (FIG. 9A) and an indirect immunofluorescence assay (FIG. 9B) showed that HepG2/bcl-2#5, a clone stably expressing bcl-2, overproduced human Bcl-2. In these experiments, the HepG2/neo#1 cell clone served as a negative control. Comparison of HepG2/bcl-2#5 cells with HepG2/neo#1 cells, showed that the overexpression of Bcl-2 did not affect the intracellular synthesis of the fusion proteins in transfected cells. The effect of bcl-2 on $M^{1-40/DEN-2}$-induced apoptosis was then investigated by monitoring changes in nuclear morphology (FIG. 9C). After 30 hours of transfection, 7% of $M^{1-40/DEN-2}$-expressing HepG2/neo#1 cells underwent apoptosis. In contrast, less than 2% of $M^{1-40/DEN-2}$-expressing HepG2/bcl-2#5 cells were apoptotic at this time. After 48 hours of transfection, $M^{1-40/DEN-2}$-expressing cells were detected among transfected HepG2/bcl-2#5 cells. Thus, M ectodomain-induced apoptosis is inhibited by overexpression of Bcl-2.

EXAMPLE 7

Expression of Dengue $M^{32-40}$ Sequence Results in Disruption of Mitochondrial Potential and Caspase Activation 1) Materials and Methods 1.1) Cell Line and Plasmids Human epithelial HeLa cell line was cultured in DMEM supplemented with 10% fetal calf serum and 2 mM L-glutamine.

Figure 11:
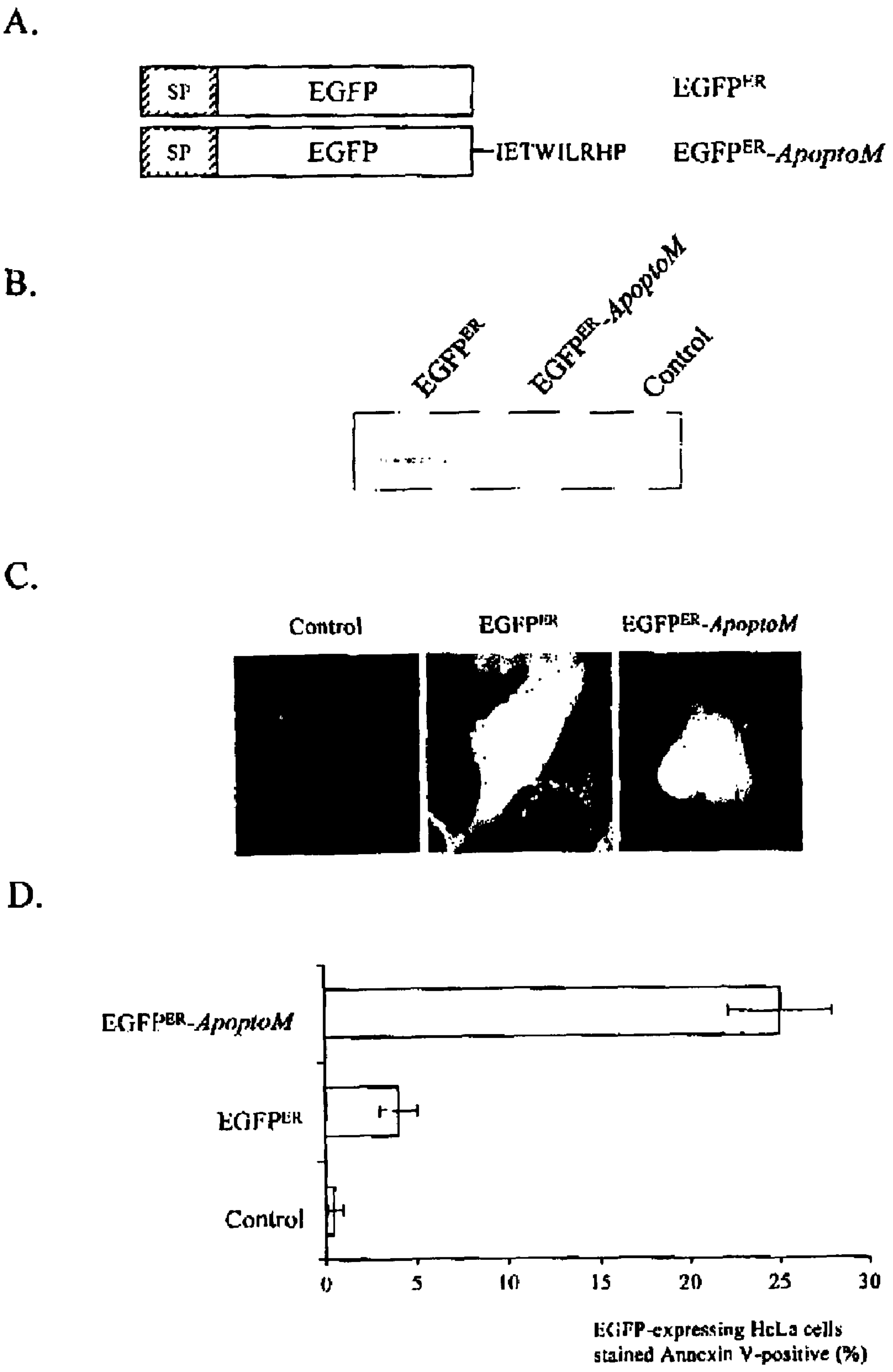

The plasmids $pC^{95-114}$-EGFP and $pC^{95-114}$-EGFP-$M^{32-40}$ are prepared as specified in Example 1. Briefly, $pC^{95-114}$-EGFP was generated by fusing the DEN-1 cDNA encoding the signal sequence MNRRKRSVTMLLMPTALA (SEQ ID NO:28) (residues C-95 to C-114) upstream from the reporter gene EGFP into the plasmid pEGFP-N1. $pC^{95-114}$-EGFP-$M^{32-40}$ was generated by fusing the DEN-2 cDNA encoding the 9-residue sequence M-32 to M-40 immediately downstream from the gene encoding EGFP. As depicted in FIG. 11A, $pC^{95-114}$-EGFP and $pC^{95-114}$-EGFP-$M^{32-40}$ express $EGFP^{ER}$ or $EGFP^{ER}$-$M^{32-40}$ respectively.

1.2) In Situ Detection of Apoptotic Cells (See Also Example 1)

Cells were distributed to Permanox Lab-tek chambers (Nalge Nunc International) and transfected with 6 μg of plasmid per $10^6$ cells in the presence of FuGene 6 transfection reagent (Roche Applied Science), according to the manufacturer's instructions. The cells were fixed by incubation with 3.2% paraformaldehyde in PBS for 20 min. Transiently-transfected cells were assayed for EGFP production by direct fluorescence analysis. We investigated the nuclear changes associated with apoptotic cell death by TUNEL method. Cells were examined under an AXIOPLAN 2 fluorescence microscope (Zeiss). Images were processed on a computer, using SimplePCI 5.1, Adobe Photoshop and Powerpoint softwares.

1.3) Flow Cytometry Analysis of Cell Death

The method of Example 4 is used.

1.4) Mitochondrial Transmembrane Potential ($\Delta\Psi_m$) Measurement and ROS (Reactive Oxygen Species) Detection For the detection of $\Delta\Psi_m$, transfected cells were labeled by incubation with 50 nM of the mitochondrial potential sensor MitoTracker Red CMXRos (Molecular Probes) in PBS for 30 min at 37° C. according to the manufacturer's instructions. Hydroethidine (HE; Molecular Probes) was employed to measure ROS. Transfected cells were incubated for 15 min at 37° C. with 2 μM of the ROS-sensitive fluorescent dye according to the manufacturer's instructions. ROS are able to oxydize HE to the fluorescent ethidium bromide (EB). The stained cells were analyzed by flow cytometry.

1.5) Western Blot Analysis

Transfected cells were harvested and washed with ice-cold PBS, and lysed in 50 μl of lysis buffer for 10 min on ice (0.5% NP-40, 0.15 M NaCl, 5.0 mM EDTA, 0.05 M Tris [pH 6.8], 1.0 mM PMSF). Lysates were cleared by centrifugation (13,000×g, 5 min), boiled for 5 min and stored at −20° C. Samples containing 40 μg of protein were subjected to 12% SDS-PAGE and transferred to PVDF membrane (Roche Applied Science). Equal protein loading was controlled by Ponceau Red (Sigma). Blots were probed with the specified primary antibodies, followed by horseradish peroxydase conjugated secondary antibodies (Amersham). Antigen-antibody complexes were visualized using the ECL detection system (Amersham).

2) Results

To investigate the molecular mechanisms by which $M^{32-40}$ induces apoptosis, the Inventors examined the death-promoting activity of $M^{32-40}$-tagged EGFP with residues M-32 to M-40 of DEN-2 virus fused downstream from the cytoplasmic EGFP. Because transport of $M^{32-40}$ through the secretory pathway is essential in the initiation of apoptosis (see Example 2), the prM translocation signal was inserted upstream from $M^{32-40}$-tagged EGFP to generate EGFP ER-$M^{32-40}$ (FIG. 11A). The fusion construct $EGFP^{ER}$ in which $M^{32-40}$ was lacking served as a control. The sequences encoding the EGFP fusion constructs have been inserted into a mammalian expression vector.

The production of the EGFP fusion constructs was examined by transient transfection of HeLa cells. The $M^{32-40}$-tagged EGFP was readily detected in HeLa cell lysates as detected by immunoblotting (FIG. 11B). However, the presence of viral sequence resulted in the production of recombinant EGFP at a lower level than that observed with control. Transfected HeLa cells were assayed for EGFP production by direct fluorescence analysis. As assessed by TUNEL method, apoptotic nuclear fragmentation in $M^{32-40}$-expressing cells after 25 h of transfection (FIG. 11C, red) was observed. The rate of early apoptosis was investigated by flow cytometry, using the Annexin V affinity assay. At 20 h of transfection, ~25% of HeLa cells producing $EGFP^{ER}$-$M^{32-40}$ were labeled with Annexin V (FIG. 11D). These results are consistent with the finding that $M^{32-40}$ is a potent inducer of apoptosis in transformed cells.

Example 6 shows that enforced expression of anti-apoptosis Bcl-2 protein abolishes the death-promoting activity of $EGFP^{ER}$-$M^{32-40}$. Thus, the viral sequence might exert its cytotoxic effects by activating a mitochondrion-dependent apoptotic pathway. The inner membrane of mitochondria is characterized by a transmembrane potential $\Delta\Psi_m$ generated through the activity of proton pump of the respiratory chain (56). There is growing evidence that mitochondrial $\Delta\Psi_m$ is altered in cells undergoing apoptosis (9). Because Bcl-2 modulates apoptosis by preventing the $\Delta\Psi_m$ loss (9, 1), the Inventors determined whether the death-promoting activity of $M^{32-40}$ involves alterations of $\Delta\Psi_m$. Transfected HeLa cells were examined by flow cytometry using the mitochondrial potential sensor CMXRos. At 20 h of transfection, expression of $M^{32-40}$ led to a significant decrease of $\Delta\Psi_m$ as compared to control (FIG. 12A), indicating that disruption of mitochondrial transmembrane occurs in $M^{32-40}$-expressing HeLa cells. It is believed that Bcl-2 can act as an antioxidant stabilizing $\Delta\Psi_m$ (9). Consistent with this notion, the Inventors investigated whether $M^{32-40}$ mediated disruption of $\Delta\Psi_m$ is accompagnied by mitochondrial generation of ROS. Production of ROS was assessed by staining transfected HeLa cells with the ROS sensitive fluorescent dye hydroethidine (HE). As a positive control, 1 μM staurosporine led a significant increase in the concentration of ROS in HeLa cells (FIG. 12B). At 20 h of transfection, there was no obvious ROS generation in transfected HeLa cells producing either $EGFP^{ER}$-$M^{32-40}$ or $EGFP^{ER}$ (FIG. 12B). It is of note that treatment of transfected HeLa cells with up to 10 mM of antioxydant N-acetyl-L-cysteine (NAC) showed no protective effect against $M^{32-40}$-induced apoptosis. These results suggest that $M^{32-40}$-triggered apoptotic pathway did not involve ROS generation.

Mitochondria membrane permeabilization plays an essential role in apoptosis, releasing caspase-activating proteins that are normally confined to the mitochondrial intermembrane space (9). Caspases are responsible for the morphological and biochemical changes associated with apoptosis (15). To assess the involvement of caspases in $M^{32-40}$-induced apoptosis, the effects of caspase inhibitors on transfected HeLa cells expressing $EGFP^{ER}$-$M^{32-40}$ were tested. Transfected cells were incubated with a final concentration of 50 μM of caspase inhibitor continuously, from transfection onwards. After 25 h of transfection, the death-promoting activity of $M^{32-40}$ was partially inhibited in HeLa cells incubated with the general caspase inhibitor z-VAD-fmk (FIG. 12C). Therefore, $M^{32-40}$-induced apoptosis depends on caspases (see Example 6).

Caspase-9 activation may play a crucial role in post-mitochondrial apoptosis, triggering proapoptotic signaling further downstream (9). Treatment with the caspase-9-specific inhibitor z-LEHD-fink did not confer protection against the death-promoting activity of $M^{32-40}$ (FIG. 12C). This finding suggests that $M^{32-40}$-induced apoptosis can be initiated through a caspase-9 independent pathway. Caspase 3 is a key effector protein that promotes apoptosis by inactivating proteins involved in DNA repair such as poly(ADP-ribose) polymerase (PARP) (15). Treatment with the caspase-3-specific inhibitor z-DEVD-fmk afforded approximately 50% protection to transfected HeLa cells against the proapoptotic activity of $EGFP^{ER}$-$M^{32-40}$ (FIG. 12C). Moreover, caspase-3-like activity was detected by assaying PARP cleavage. As a positive control, HeLa cells were treated with 1 μM staurosporine. At 20 h of transfection, the appearance of the 85 kDa-caspase cleaved product of PARP (116 kDa) in HeLa cells producing $EGFP^{ER}$-$M^{32-40}$, as assessed by immunoblotting (FIG. 12D) was not observed, whereas PARP was not cleaved in $EGFP^{ER}$-expressing cells. These results suggest that caspase-3 participates in $M^{32-40}$-induced apoptosis.

REFERENCES

1. Adams J. M. et al., *Trends Biochem. Sci.*, 2001, 26: 61–66.
2. Adrain C. et al., *Trends Biochem. Sci.*, 2001, 26:390–397.
3. Bray M. et al., *Virology,* 1991, 185: 505–508.
4. Burns T. F. et al., *J. Cell. Physiol.*, 1999, 181: 231–239.
5. Chambers T. J. et al., *Annu. Rev. Microbiol.*, 1990, 44: 649–688.
6. Cocquerel L. et al., *J. Virol.*, 1999, 73: 2641–2649.
7. Courageot M-P. et al., *J. Virol.*, 2000, 74: 564–572.
8. Couvelard A. et al., *Hum. Pathol.*, 1999, 30: 1106–1110.
9. Desagher S. et al., *Trends Cell Biol.*, 2000, 10: 369–377.
10. Despres P. et al., *J. Gen. Virol.*, 1987, 68: 2245–2247.
11. Despres P. et al., *Virology,* 1993, 196: 209–219.
12. Despres P. et al., *J. Virol.*, 1996, 70: 4090–4096.
13. Despres P. et al., *J. Virol.*, 1998, 72: 823–829.
14. Duarte dos Santos C. N. et al., *Virology,* 2000, 274: 292–308.
15. Eamshaw W. C. et al., *Annu. Rev. Biochem.*, 1999, 68: 383–424.
16. Fearnhead H. O. et al., *Genes Dev.*, 1997, 11: 1266–1276.
17. Ferry, K. F. et al., *Nature Cell. Biol.*, 2001, 3: 255–263.
18. Gluzman Y., *Cell,* 1981, 23: 175–182.
19. Grabenhorst E. et al., *J. Biol. Chem.*, 1999, 274: 36107–36116.
20. Hahn, C. S. et al., *Proc. Natl. Acad. Sci.*, 1987, 84: 2019–2023.
21. Hengartner M. O., *Nature,* 2000, 407: 770–776.

22. Jan, J-T. et al., *J. Virol.,* 2000, 74: 8680–8691.
23. Jürgensmeier J. M. et al., *Natl. Acad. Sci.,* 1998, 95: 4997–5002.
24. Kimura K. et al., *Vitam. Horm.,* 2000, 58: 257–266.
25. Kuhn R. J. et al., *Cell,* 2002, 108: 717–725.
26. Kuwana T. et al., *Cell,* 2002, 111: 331–342.
27. Li P. et al., *Cell,* 1997, 91: 479–489.
28. Liao C-L. et al., *J. Virol.,* 1997, 71: 5963–5971.
29. Liao C-J. et al., *J. Virol.,* 1998, 72: 9844–9854.
30. Lin, Y-L. et al., *J. Med. Virol.,* 2000, 60: 425–431.
31. Lomonosova E. et al., *J. Virol.,* 2002, 76: 11283–11290.
32. Louis N. et al., *Virology,* 1997, 233: 423–429.
33. Marianneau P. et al., *J. Virol.,* 1997, 71: 3244–3249.
34. Marianneau P. et al., *J. Infect. Dis.,* 1998, 178: 1270–1278.
35. Monath T. P., 1999, Yellow fever virus (Flaviviridae), p1979–1986. In Encyclopedia of Virology, $2^d$ ed. Editors: Granoff, A. and Webster, R. G. Academic Press.
36. Parquet M. D. C. et al., *FEBS Lett.,* 2001, 500: 17–24.
37. Parquet M. C. et al., *Arch. Virol.,* 2002, 147: 1105–1119.
38. Pelham H. R., *Cell Struct. Funct.,* 1996, 21: 413–419.
39. Prikhod'ko G. G. et al., *Virology,* 2001, 286: 328–335.
40. Prikhod'ko G. G. et al., *J. Virol.,* 2002, 76: 5701–5710.
41. Rice C. M., 1996, Flaviviridae: the viruses and their replication, p.931–959. In Fields virology, $3^d$ ed. Editors: Fields, B. N., Knipe, D. M., Howley, P. M., et al. Lippincott-Raven Publishers, Philadelphia.
42. Roulston, A. et al., *Annu. Rev. Microbiol.,* 1999, 53, 577–628.
43. Slee E. A. et al., *J. Cell. Biol.,* 1999, 144: 281–292.
44. Su H-L. et al., *Virology,* 2001, 282: 141–153.
45. Su H-L. et al., *J. Virol.,* 2002, 76: 4162–4171.
46. Tsai S—C. et al., *J. Biol. Chem.,* 2000, 275: 3239–3246.
47. Vazquez S. et al., *Vaccine,* 2002, 20: 1823–1830.
48. White E., *Oncogene,* 2001, 20: 7836–7846.
49. Wang E. et al., *J. Gen. Virol.,* 1995, 76: 2749–2755.
50. Xiao S-Y. et al., *J. Infect. Dis.,* 2001, 183: 1437–1444.
51. Yang J. et al., *Science,* 1997, 275: 1129–1132.
52. Ying H. et al., *J. Immunol.,* 1995, 154: 2743–2752.
53. Higgins D. et al., *Nucleic Acids Res.,* 1994, 22, 4673–4680.
54. R. Lopez et al., *The Clustal WWW server at the EBI-embnet.news,* 1997, 4.2.
55. B. Levine et al., *Nature,* 1993, 361(6414), 739–42.
56. L. Ravagnan et al., *J. Cell. Physiol.,* 2002, 192, 131–137.

The invention claimed is:

1. An isolated polypeptide having the following formula:

X1-X2-X3-X4-X5-X6-X7-X8-X9, wherein:

X1 is absent or represents an amino acid selected from the group consisting of non-charged polar amino acids and non-polar amino acids, X2 is absent or represents an amino acid selected from the group consisting of acidic amino acids, non-charged polar amino acids and non-polar amino acids, X3 is selected from the group consisting of basic amino acids, non-charged polar amino acids and non-polar amino acids, X4 is W, X5 represents an amino acid selected from the group consisting of A, V, L, I, P, W, M and C, X6 is selected from the group consisting of non-polar amino acids, X7 is a basic amino acid X8 is selected from the group consisting of basic amino acids and non-charged polar amino acids and X9 is absent or represents an amino acid selected from the group consisting of basic amino acids and non-polar amino acids.

2. The isolated polypeptide according to claim 1, wherein said polypeptide is selected from the group consisting of the following pro-apoptotic polypeptides:

polypeptides of 6–9 amino acids wherein X5=I, L, A;

polypeptides of 6–9 amino acids, wherein X1 is absent or represents I, V, T, X2 is absent or represents E, X3=T, S, R, N, X4=W, X5=I, A, X6=L, V, X7=R, X8=H, N, X9 is absent or represents P; and polypeptides of 6–9 amino acids, wherein X3=T, X5=I, X6=L and X8=H.

3. The isolated polypeptide according to claim 1, wherein said polypeptide is selected from the group consisting of the following pro-apoptotic polypeptides:

polypeptides of 6–9 amino acids wherein X5=I, L, A;

polypeptides of 6–9 amino acids, wherein X1 is absent or represents I, V, T, X2 is absent or represents E, X3=T, S, R, N, X4=W, X5=I, A, X6=L, V, X7=R, X8=H, N, X9 is absent or represents P; and polypeptides of 6–9 amino acids, wherein X3=T, X5=I, X6=L and X8=H, with the proviso that said polypeptide is not the polypeptide having the following sequence: IETWILRHP (SEQ ID NO.:29.

4. The isolated polypeptide according to claim 1, wherein said polypeptide has the following sequence: IETWILRHP.

5. The isolated polypeptide according to claim 1, wherein said polypeptide is associated with or conjugated to another polypeptide or protein such as a carrier protein or non-peptide molecule and/or incorporated into a suitable support.

6. A method of screening for molecules capable of modulating apoptosis comprising:

introducing one or more polypeptides according to claim 1 into a cell, contacting said cell with the molecule to be screened and detecting the presence or absence of apoptosis.

7. The new polypeptide according to claim 5 wherein the protein with which the polypeptide is associated is a carrier protein.

* * * * *

```
                        SEQUENCE LISTING

<160> NUMBER OF SEQ ID NOS: 40

<210> SEQ ID NO 1
<211> LENGTH: 45
<212> TYPE: DNA
<213> ORGANISM: Artificial sequence
<220> FEATURE:
<223> OTHER INFORMATION: 5' primer for M1-40/DEN-1

<400> SEQUENCE: 1

gacaaacgtt ccgtggctct gtgacacacg tgggacttgg tctag                    45


<210> SEQ ID NO 2
<211> LENGTH: 33
<212> TYPE: DNA
<213> ORGANISM: Artificial sequence
<220> FEATURE:
<223> OTHER INFORMATION: 3' primer for M1-40/DEN-1

<400> SEQUENCE: 2

ctattcccag cggccgctag gccattgatg gtg                                 33


<210> SEQ ID NO 3
<211> LENGTH: 35
<212> TYPE: DNA
<213> ORGANISM: Artificial sequence
<220> FEATURE:
<223> OTHER INFORMATION: 5' primer for M1-40/DEN-2

<400> SEQUENCE: 3

cacagaagac tgtacagatc agtggcactc gttcc                               35


<210> SEQ ID NO 4
<211> LENGTH: 35
<212> TYPE: DNA
<213> ORGANISM: Artificial sequence
<220> FEATURE:
<223> OTHER INFORMATION: 3' primer for M1-40/DEN-2

<400> SEQUENCE: 4
```

-continued atattcctag cggccgctat gtcattgaag gagcg 35

<210> SEQ ID NO 5
<211> LENGTH: 42
<212> TYPE: DNA
<213> ORGANISM: Artificial sequence
<220> FEATURE:
<223> OTHER INFORMATION: 5' primer for M1-40/DEN-3

<400> SEQUENCE: 5
agacgcgtgt acagatcagt ggcgttagct ccccatgtcg cc 42

<210> SEQ ID NO 6
<211> LENGTH: 43
<212> TYPE: DNA
<213> ORGANISM: Artificial sequence
<220> FEATURE:
<223> OTHER INFORMATION: 3' primer for M1-40/DEN-3

<400> SEQUENCE: 6
gtttccgcgg ccgccacatc ttcatgtcat aggtggggta acc 43

<210> SEQ ID NO 7
<211> LENGTH: 40
<212> TYPE: DNA
<213> ORGANISM: Artificial sequence
<220> FEATURE:
<223> OTHER INFORMATION: 5' primer for M1-40/DEN-4

<400> SEQUENCE: 7
agacgagtgt acagctcagt agctttaaca ccacattcgg 40

<210> SEQ ID NO 8
<211> LENGTH: 42
<212> TYPE: DNA
<213> ORGANISM: Artificial sequence
<220> FEATURE:
<223> OTHER INFORMATION: 3' primer for M1-40/DEN-4

<400> SEQUENCE: 8
tgtttccgcg gccgccgcat cgtcatccgt aggatggggc ga 42

<210> SEQ ID NO 9
<211> LENGTH: 44
<212> TYPE: DNA
<213> ORGANISM: Artificial sequence
<220> FEATURE:
<223> OTHER INFORMATION: 5' primer for M1-40/JE

<400> SEQUENCE: 9
aagcgaatgt acagatccgt gtcggtccaa acacatgggg agag 44

<210> SEQ ID NO 10
<211> LENGTH: 43
<212> TYPE: DNA
<213> ORGANISM: Artificial sequence
<220> FEATURE:
<223> OTHER INFORMATION: 3' primer for M1-40/JE

<400> SEQUENCE: 10
attgccgcgg ccgcgacaat ttcaactgta agccggagcg acc 43

<210> SEQ ID NO 11
<211> LENGTH: 30
<212> TYPE: DNA

-continued

<213> ORGANISM: Artificial sequence
<220> FEATURE:
<223> OTHER INFORMATION: 5' primer for M1-40/WN

<400> SEQUENCE: 11
agacgcatgt acaggtcact gacagtgcag 30

<210> SEQ ID NO 12
<211> LENGTH: 30
<212> TYPE: DNA
<213> ORGANISM: Artificial sequence
<220> FEATURE:
<223> OTHER INFORMATION: 3' primer for M1-40/WN

<400> SEQUENCE: 12
cattccgcgg ccgctctagc tgtaagctgg 30

<210> SEQ ID NO 13
<211> LENGTH: 43
<212> TYPE: DNA
<213> ORGANISM: Artificial sequence
<220> FEATURE:
<223> OTHER INFORMATION: 5' primer for M1-40/YF

<400> SEQUENCE: 13
aggaggttgt acagggccat tgacttgcct acgcatgaaa acc 43

<210> SEQ ID NO 14
<211> LENGTH: 43
<212> TYPE: DNA
<213> ORGANISM: Artificial sequence
<220> FEATURE:
<223> OTHER INFORMATION: 3' primer for M1-40/YF

<400> SEQUENCE: 14
tgtcagtgcg gccgctgcag tgtcatgagt aggccggacc aac 43

<210> SEQ ID NO 15
<211> LENGTH: 23
<212> TYPE: DNA
<213> ORGANISM: Artificial sequence
<220> FEATURE:
<223> OTHER INFORMATION: 5' primer for M1-30/DEN-2, M1-20/DEN-2 and M9-30/DEN-2

<400> SEQUENCE: 15
ttttggcagt acatcaatgg gcg 23

<210> SEQ ID NO 16
<211> LENGTH: 38
<212> TYPE: DNA
<213> ORGANISM: Artificial sequence
<220> FEATURE:
<223> OTHER INFORMATION: 3' primer for M1-30/DEN-2 and M9-30/DEN-2

<400> SEQUENCE: 16
aagatcgcgg ccgcaattca ctggacatgt ttccaggc 38

<210> SEQ ID NO 17
<211> LENGTH: 40
<212> TYPE: DNA
<213> ORGANISM: Artificial sequence
<220> FEATURE:
<223> OTHER INFORMATION: 3' primer for M1-20/DEN-2

<400> SEQUENCE: 17

-continued tttccgcggc cgctctgatc acatccatgt ttcagttcag 40

<210> SEQ ID NO 18
<211> LENGTH: 34
<212> TYPE: DNA
<213> ORGANISM: Artificial sequence
<220> FEATURE:
<223> OTHER INFORMATION: 5' primer for M9-40/DEN-2

<400> SEQUENCE: 18
tggttctgta catgggaatg ggactggaga cacg 34

<210> SEQ ID NO 19
<211> LENGTH: 24
<212> TYPE: DNA
<213> ORGANISM: Artificial sequence
<220> FEATURE:
<223> OTHER INFORMATION: 3' primer for M9-40/DEN-2, M20-40/DEN-2 and
M32-40/DEN-2

<400> SEQUENCE: 19
tcttgcagtt cattcagggc accg 24

<210> SEQ ID NO 20
<211> LENGTH: 33
<212> TYPE: DNA
<213> ORGANISM: Artificial sequence
<220> FEATURE:
<223> OTHER INFORMATION: 5' primer for M20-40/DEN-2

<400> SEQUENCE: 20
actgaaatgt acatgtcatc agaaggggcc tgg 33

<210> SEQ ID NO 21
<211> LENGTH: 31
<212> TYPE: DNA
<213> ORGANISM: Artificial sequence
<220> FEATURE:
<223> OTHER INFORMATION: 5' primer for M32-40/DEN-2

<400> SEQUENCE: 21
atgtcctgta cattgaaact tggatcttga g 31

<210> SEQ ID NO 22
<211> LENGTH: 31
<212> TYPE: DNA
<213> ORGANISM: Artificial sequence
<220> FEATURE:
<223> OTHER INFORMATION: 5' primer for M1-40/DEN-1 followed by the
transmembrane domain of mouse CD72

<400> SEQUENCE: 22
tgctggagga atagcagtct taaaaattgg c 31

<210> SEQ ID NO 23
<211> LENGTH: 29
<212> TYPE: DNA
<213> ORGANISM: Artificial sequence
<220> FEATURE:
<223> OTHER INFORMATION: 3' primer for M1-40/DEN-1 followed by the
transmembrane domain of mouse CD72

<400> SEQUENCE: 23
tattggtggc ttcccaaatc ctggtcccc 29

<210> SEQ ID NO 24

-continued

<211> LENGTH: 29
<212> TYPE: DNA
<213> ORGANISM: Artificial sequence
<220> FEATURE:
<223> OTHER INFORMATION: 3' primer for M1-40/DEN-1 followed by the transmembrane domain of mouse CD72

<400> SEQUENCE: 24
agacacccgg ggatagagaa ctcccaggc 29

<210> SEQ ID NO 25
<211> LENGTH: 54
<212> TYPE: DNA
<213> ORGANISM: Artificial sequence
<220> FEATURE:
<223> OTHER INFORMATION: 3' primer for M1-40/DEN-1 followed by the KDEL motif

<400> SEQUENCE: 25
taaagcggcc gctcacaact cgtcttttgg gtgtctcaaa gcccaagtct ccac 54

<210> SEQ ID NO 26
<211> LENGTH: 44
<212> TYPE: DNA
<213> ORGANISM: Artificial sequence
<220> FEATURE:
<223> OTHER INFORMATION: 3' primer for mutant protein C95-114-EGFP-M1-40/YF.wt

<400> SEQUENCE: 26
agagtcgcgg ccgcaaatca ggggttcctc accaaccatc tctc 44

<210> SEQ ID NO 27
<211> LENGTH: 61
<212> TYPE: DNA
<213> ORGANISM: Artificial sequence
<220> FEATURE:
<223> OTHER INFORMATION: 3' primer for mutant protein C95-114-EGFP-M1-40/YF.17D (T34, I36, L37, H39)

<400> SEQUENCE: 27
agagtcgcgg ccgcaaatca ggggtgcctc aggatccatg tctcaatctt ttggagttgc 60
c 61

<210> SEQ ID NO 28
<211> LENGTH: 18
<212> TYPE: PRT
<213> ORGANISM: Dengue virus type 1
<220> FEATURE:
<221> NAME/KEY: misc_feature
<223> OTHER INFORMATION: Signal sequence

<400> SEQUENCE: 28

Met Asn Arg Arg Lys Arg Ser Val Thr Met Leu Leu Met Pro Thr Ala
1 5 10 15

Leu Ala

<210> SEQ ID NO 29
<211> LENGTH: 9
<212> TYPE: PRT
<213> ORGANISM: Dengue virus type 2
<220> FEATURE:
<221> NAME/KEY: misc_feature
<223> OTHER INFORMATION: Peptide of the M protein confering apoptotic activity

<400> SEQUENCE: 29

-continued

```
Ile Glu Thr Trp Ile Leu Arg His Pro
1               5


<210> SEQ ID NO 30
<211> LENGTH: 33
<212> TYPE: DNA
<213> ORGANISM: Artificial sequence
<220> FEATURE:
<223> OTHER INFORMATION: 5' primer for M1-40/DEN-1 followed by the
      transmembrane domain of mouse CD72

<400> SEQUENCE: 30

gaggcggcta gcgctatggc tgacgctatc acg                                 33


<210> SEQ ID NO 31
<211> LENGTH: 40
<212> TYPE: PRT
<213> ORGANISM: Dengue virus type 2
<220> FEATURE:
<221> NAME/KEY: misc_feature
<223> OTHER INFORMATION: M1-40/DEN-2

<400> SEQUENCE: 31

Ser Val Ala Leu Val Pro His Val Gly Met Gly Leu Glu Thr Arg Thr
1               5                   10                  15

Glu Thr Trp Met Ser Ser Glu Gly Ala Trp Lys His Val Gln Arg Ile
            20                  25                  30

Glu Thr Trp Ile Leu Arg His Pro
        35                  40


<210> SEQ ID NO 32
<211> LENGTH: 30
<212> TYPE: PRT
<213> ORGANISM: Dengue virus type 2
<220> FEATURE:
<221> NAME/KEY: misc_feature
<223> OTHER INFORMATION: M1-30/DEN-2

<400> SEQUENCE: 32

Ser Val Ala Leu Val Pro His Val Gly Met Gly Leu Glu Thr Arg Thr
1               5                   10                  15

Glu Thr Trp Met Ser Ser Glu Gly Ala Trp Lys His Val Gln
            20                  25                  30


<210> SEQ ID NO 33
<211> LENGTH: 20
<212> TYPE: PRT
<213> ORGANISM: Dengue virus type 2
<220> FEATURE:
<221> NAME/KEY: misc_feature
<223> OTHER INFORMATION: M1-20/DEN-2

<400> SEQUENCE: 33

Ser Val Ala Leu Val Pro His Val Gly Met Gly Leu Glu Thr Arg Thr
1               5                   10                  15

Glu Thr Trp Met
            20


<210> SEQ ID NO 34
<211> LENGTH: 22
<212> TYPE: PRT
<213> ORGANISM: Dengue virus type 2
<220> FEATURE:
<221> NAME/KEY: misc_feature
<223> OTHER INFORMATION: M9-30/DEN-2
```

-continued

```
<400> SEQUENCE: 34

Gly Met Gly Leu Glu Thr Arg Thr Glu Thr Trp Met Ser Ser Glu Gly
1               5                   10                  15

Ala Trp Lys His Val Gln
            20


<210> SEQ ID NO 35
<211> LENGTH: 32
<212> TYPE: PRT
<213> ORGANISM: Dengue virus type 2
<220> FEATURE:
<221> NAME/KEY: misc_feature
<223> OTHER INFORMATION: M9-40/DEN-2

<400> SEQUENCE: 35

Gly Met Gly Leu Glu Thr Arg Thr Glu Thr Trp Met Ser Ser Glu Gly
1               5                   10                  15

Ala Trp Lys His Val Gln Arg Ile Glu Thr Trp Ile Leu Arg His Pro
            20                  25                  30


<210> SEQ ID NO 36
<211> LENGTH: 21
<212> TYPE: PRT
<213> ORGANISM: Dengue virus type 2
<220> FEATURE:
<221> NAME/KEY: misc_feature
<223> OTHER INFORMATION: M20-40/DEN-2

<400> SEQUENCE: 36

Met Ser Ser Glu Gly Ala Trp Lys His Val Gln Arg Ile Glu Thr Trp
1               5                   10                  15

Ile Leu Arg His Pro
            20


<210> SEQ ID NO 37
<211> LENGTH: 40
<212> TYPE: PRT
<213> ORGANISM: Yellow fever virus
<220> FEATURE:
<221> NAME/KEY: misc_feature
<223> OTHER INFORMATION: M1-40/YF.17D

<400> SEQUENCE: 37

Ala Ile Asp Leu Pro Thr His Glu Asn His Gly Leu Lys Thr Arg Gln
1               5                   10                  15

Glu Lys Trp Met Thr Gly Arg Met Gly Glu Arg Gln Leu Gln Lys Ile
            20                  25                  30

Glu Arg Trp Phe Val Arg Asn Pro
        35                  40


<210> SEQ ID NO 38
<211> LENGTH: 40
<212> TYPE: PRT
<213> ORGANISM: Dengue virus type 1
<220> FEATURE:
<221> NAME/KEY: misc_feature
<223> OTHER INFORMATION: M1-40/DEN-1

<400> SEQUENCE: 38

Ser Val Ala Leu Ala Pro His Val Gly Leu Gly Leu Glu Thr Arg Thr
1               5                   10                  15

Glu Thr Trp Met Ser Ser Glu Gly Ala Trp Lys Gln Ile Gln Lys Val
            20                  25                  30
```

-continued

```
Glu Thr Trp Ala Leu Arg His Pro
        35                  40


<210> SEQ ID NO 39
<211> LENGTH: 31
<212> TYPE: PRT
<213> ORGANISM: Dengue virus type 1
<220> FEATURE:
<221> NAME/KEY: misc_feature
<223> OTHER INFORMATION: Sub-sequence of 31 aminoacids of M1-40/DEN-1

<400> SEQUENCE: 39

Ser Val Ala Leu Ala Pro His Val Gly Leu Gly Leu Glu Thr Arg Thr
1               5                   10                  15

Glu Thr Trp Met Ser Ser Glu Gly Ala Trp Lys Gln Ile Gln Lys
            20                  25                  30


<210> SEQ ID NO 40
<211> LENGTH: 9
<212> TYPE: PRT
<213> ORGANISM: Dengue virus type 1
<220> FEATURE:
<221> NAME/KEY: misc_feature
<223> OTHER INFORMATION: Subsequence of 9 aminoacids of M1-40/DEN-1

<400> SEQUENCE: 40

Val Glu Thr Trp Ala Leu Arg His Pro
1               5
```